(12) United States Patent
Vetter et al.

(10) Patent No.: US 11,440,010 B2
(45) Date of Patent: Sep. 13, 2022

(54) TANGENTIAL VIRAL FILTRATION

(71) Applicant: Genzyme Corporation, Cambridge, MA (US)

(72) Inventors: Tarl Vetter, Framingham, MA (US); Kevin Brower, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 17/643,113

(22) Filed: Dec. 7, 2021

(65) Prior Publication Data
US 2022/0088602 A1 Mar. 24, 2022

Related U.S. Application Data

(63) Continuation of application No. 16/815,657, filed on Mar. 11, 2020.

(60) Provisional application No. 62/816,786, filed on Mar. 11, 2019.

(51) Int. Cl.
*B01L 3/00* (2006.01)
*C12M 1/00* (2006.01)

(52) U.S. Cl.
CPC ....... *B01L 3/502753* (2013.01); *C12M 47/12* (2013.01); *B01L 2300/044* (2013.01); *B01L 2300/0681* (2013.01); *B01L 2300/0861* (2013.01)

(58) Field of Classification Search
None
See application file for complete search history.

(56) References Cited

U.S. PATENT DOCUMENTS

| | | | |
|---|---|---|---|
| 2003/0229212 A1* | 12/2003 | Fahrner | C07K 1/34 530/417 |
| 2006/0252054 A1 | 11/2006 | Lin et al. | |
| 2012/0258459 A1 | 10/2012 | Huang | |
| 2020/0290044 A1 | 9/2020 | Vetter et al. | |

FOREIGN PATENT DOCUMENTS

| | | |
|---|---|---|
| CA | 1318088 | 5/1993 |
| WO | WO 2013/192009 | 12/2013 |
| WO | WO 2018/035116 | 2/2018 |
| WO | WO 2018/230397 | 12/2018 |

OTHER PUBLICATIONS

International Preliminary Report on Patentability in Application No. PCT/US/2020/021979, dated Aug. 25, 2021, 9 pages.
International Search Report and Written Opinion in Application No. PCT/US2020/021979, dated Jun. 18, 2020, 11 pages.

\* cited by examiner

*Primary Examiner* — Lore R Jarrett
(74) *Attorney, Agent, or Firm* — Fish & Richardson P.C.

(57) ABSTRACT

Viral filters include a filter member featuring a first surface and a second surface and having a thickness extending between the first and second surfaces in a first direction, and a plurality of channels formed in the filter member, each of the channels having a channel axis, where during use, a solution carrying a viral load flows in a direction parallel to the first surface, and at least a portion of the viral load enters the membrane through the first surface and propagates in the first direction, and where for at least 50% of the channels in the filter member, the channel axis is oriented at an angle of between 5 degrees and 85 degrees relative to the first direction.

20 Claims, 10 Drawing Sheets

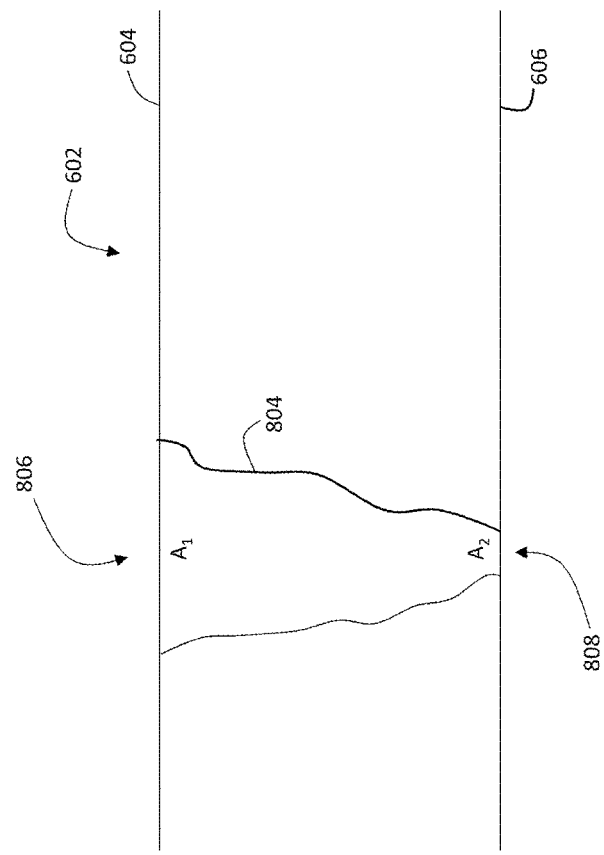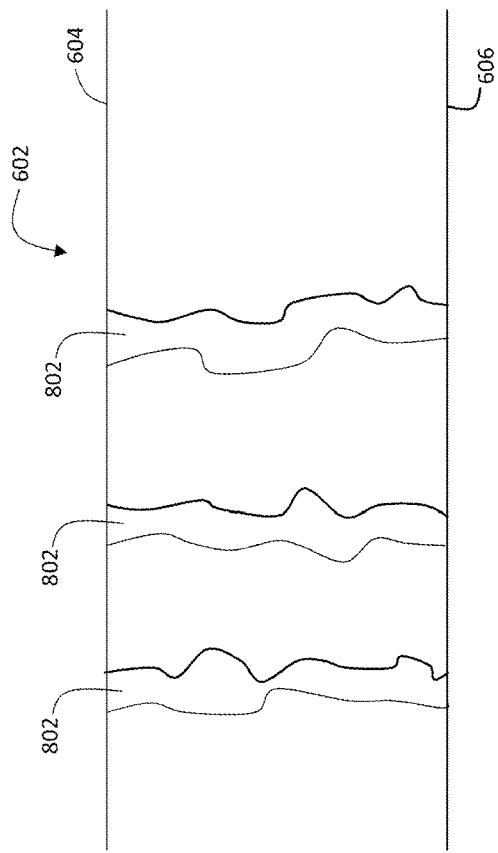

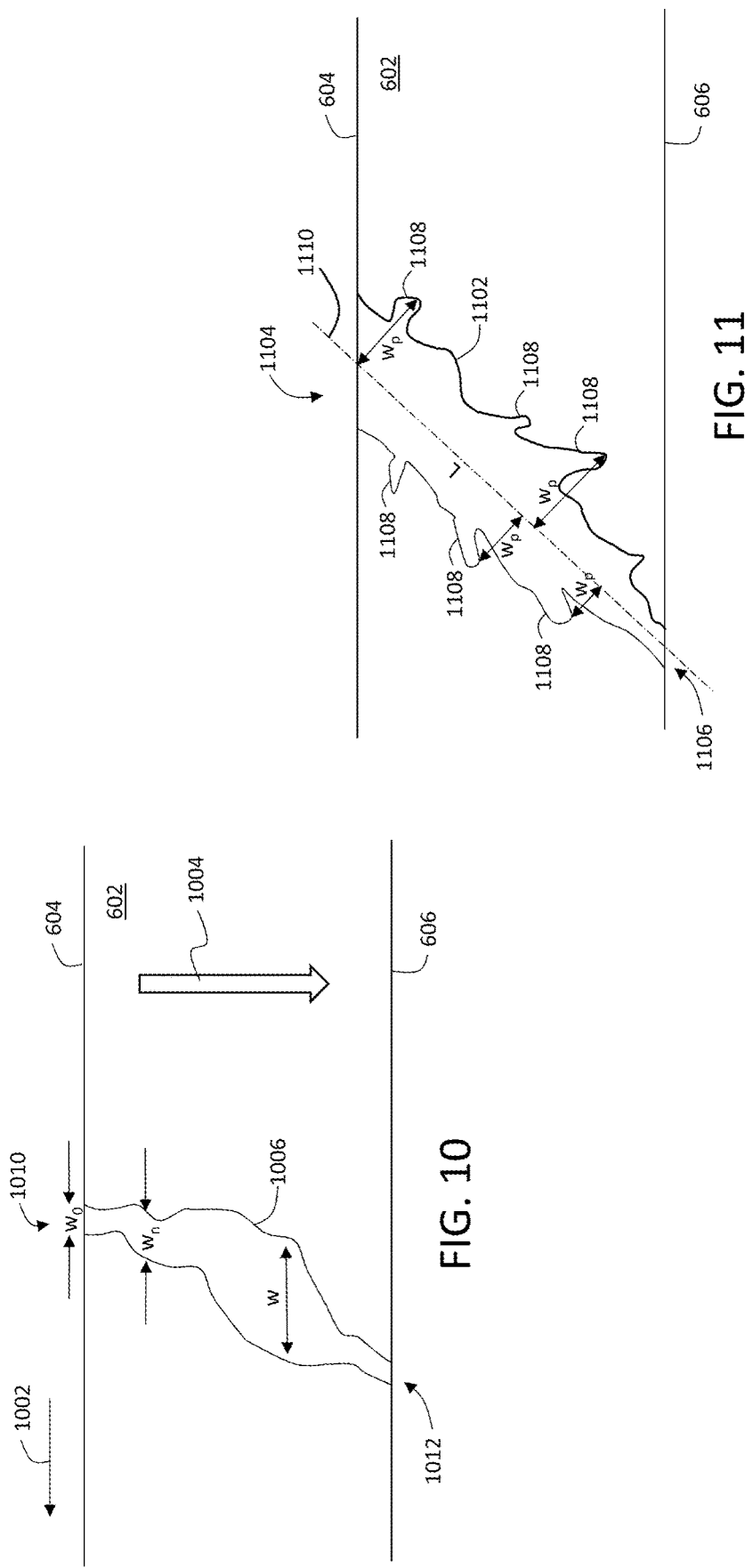

TANGENTIAL VIRAL FILTRATION

CROSS-REFERENCE TO RELATED APPLICATIONS

This application is a continuation of U.S. patent application Ser. No. 16/815,657, filed on Mar. 11, 2020, which claims priority to U.S. Provisional Patent Application No. 62/816,786, filed on Mar. 11, 2019, the entire contents of which are incorporated herein by reference.

TECHNICAL FIELD

This disclosure relates to biotechnology and biomanufacturing.

BACKGROUND OF THE INVENTION

Mammalian cells containing a nucleic acid that encodes a recombinant protein are often used to produce therapeutically or commercially important proteins. In the current environment of diverse product pipelines, biotechnology companies are increasingly driven to develop innovative solutions for highly flexible and cost-effective manufacturing of therapeutic protein drug substances.

SUMMARY

To perform biomanufacturing on a production scale, a number of unit operations are implemented as continuous processes. Among these processes, virus removal from product streams remains a challenging operation to perform. The present disclosure features systems and methods for implementing tangential flow virus filtration (TFVF). TFVF can, in some embodiments, be performed on a continuous or semi-continuous basis to permit on-line purification of a wide variety of therapeutic protein drug substances, including recombinant therapeutic protein substances. In TFVF systems, a fluid (e.g., a process fluid that includes one or more products to be purified) can be circulated through a fluid circuit that includes a filter element, which traps or retains viral particles. A portion of fluid and its contents does not pass through the filter and is re-circulated for another pass through the system.

In one aspect, the disclosure features a viral filter that includes a filter member featuring a first surface and a second surface and having a thickness extending between the first and second surfaces in a first direction, and a plurality of channels formed in the filter member, each of the channels having a channel axis, where during use, a solution carrying a viral load flows in a direction parallel to the first surface, and at least a portion of the viral load enters the membrane through the first surface and propagates in the first direction, and where for at least 50% of the channels in the filter member, the channel axis is oriented at an angle of between 5 degrees and 85 degrees relative to the first direction.

Embodiments of the filters can include any one or more of the following features.

The channel axis is oriented at an angle of between 5 degrees and 75 degrees (e.g., between 10 degrees and 60 degrees) relative to the first direction. For at least 70% of the channels (e.g., for at least 90% of the channels) in the filter member, the channel axis can be oriented at an angle of between 5 degrees and 85 degrees relative to the first direction.

The thickness of the filter member can be 150 micrometers or greater (e.g., 300 micrometers or greater, 500 micrometers or greater). Each member of the plurality of channels can include an opening at the first surface, and a ratio of a total area of the openings to a total area of the first surface can be 0.10 or more (e.g., 0.20 or more, 0.30 or more). Each member of the plurality of channels can have a volume, and a ratio of a total volume of the channels to a total volume of the member can be 0.05 or more (e.g., 0.10 or more, 0.20 or more).

For each of at least some members of the plurality of channels, the member channel includes an opening at the first surface having a first cross-sectional area in the first surface, and the first cross-sectional area can be smaller than a second cross-sectional area of the member channel at a location between the first and second surfaces. A ratio of the first cross-sectional area to the second cross-sectional area can be 0.95 or less (e.g., 0.85 or less, 0.75 or less). The at least some members can include at least 40% (e.g., at least 60%, all) of the members of the plurality of channels.

The channel axes of the plurality of channels can have a distribution of orientations relative to the first direction. An average orientation of the distribution can be between 10 degrees and 30 degrees (e.g., between 30 degrees and 50 degrees, between 50 degrees and 80 degrees) relative to the first direction. A full width at half maximum (FWHM) value of the distribution of orientations can be 60 degrees or less (e.g., 40 degrees or less, 15 degrees or less).

For each of at least some members of the plurality of channels, the member channel can include one or more secondary channels extending from the channel axis. The one or more secondary channels can extend along a secondary axis from the channel axis at an angle of between 10 degrees and 80 degrees relative to the channel axis. The one or more secondary channels can extend along a secondary axis from the channel axis at an angle of between 50 degrees and 90 degrees relative to the channel axis.

One or more of the member channels can include 3 or more (e.g., 5 or more) secondary channels. The member channels can include an average of 5 or more (e.g., 7 or more) secondary channels.

For each of at least some members of the plurality of channels, the member channel can include an opening at the first surface having a first cross-sectional area in the first surface, and a maximum cross-sectional area at a location between the first and second surfaces that is different from the first cross-sectional area. A ratio of the first cross-sectional area to the maximum cross-sectional area can be 0.50 or less (e.g., 0.30 or less, 0.10 or less).

The at least some members of the plurality of channels can include 50% or more (e.g., 80% or more) of the plurality of channels. For each of at least some members of the plurality of channels, the member channel can include a maximum cross-sectional area and a minimum cross-sectional area at different locations along the channel axis, and a ratio of the minimum cross-sectional area to the maximum cross-sectional area can be 0.75 or less (e.g., 0.50 or less, 0.30 or less).

The first surface can be planar and can have a maximum dimension measured in the plane, and a ratio of the maximum dimension to the thickness can be 10 or more (e.g., 20 or more). A porosity of the member can be between 0.3 and 0.9.

The member can be formed from a first material, and each of at least some members of the plurality of channels can include a second material positioned on an interior surface of the member channel. The first material can be selected from the group consisting of polyvinylidene difluoride (PVDF), hydrophilized PVDF, and regenerated cellulose. The second material can be selected from the group consisting of cellulose, polyethersulfones, and polyethyleneglycols.

A ratio of an average thickness of the second material on the interior surface of the member channel to a maximum cross-sectional dimension of the member channel can be 0.2 or less (e.g., 0.1 or less, 0.05 or less, 0.02 or less).

The plurality of channels can be a first plurality of channels, and the filter member can include a first layer featuring the first plurality of channels, and a second layer featuring a second plurality of channels. The second layer can contact the first layer. At least some members of the first plurality of channels can be in fluid communication with at least some members of the second plurality of channels at an interface between the first and second layers.

Each of the channels of the second plurality of channels can include a channel axis, and for at least 50% of the second plurality of channels in the second layer, the channel axis can be oriented at an angle of between 5 degrees and 90 degrees relative to the first direction. An average orientation of the first plurality of channels relative to the first direction can be different from an average orientation of the second plurality of channels relative to the first direction.

An average angle between the channel axis and the first direction can be larger than an average angle between the channel axis and the first direction for the first plurality of channels. For the second plurality of channels, an average angle between the channel axis and the first direction can be smaller than an average angle between the channel axis and the first direction for the first plurality of channels.

The first layer can be formed from a first material selected from the group consisting of polyvinylidene difluoride (PVDF), hydrophilized PVDF, and regenerated cellulose, and the second layer can be formed from a second material selected from the group consisting of celluloses and regenerated celluloses, polyethersulfones, polyethyleneglycols, polyethylenes, polypropylenes, polyvinyl benzenes, polypropylene glycols, polyurethanes, polymethyl methacrylates, and polyacrylic acids. The first and second materials can be different.

At least some channels of the first plurality of channels can include a coating material on an interior surface of the at least some channels. The coating material can be selected from the group consisting of cellulose, polyethersulfones, and polyethyleneglycols. At least some channels of the second plurality of channels can include a coating material on an interior surface of the at least some channels. The coating material can be selected from the group consisting of cellulose, polyethersulfones, and polyethyleneglycols. At least some channels of the first plurality of channels can include a first coating material on an interior surface of the at least some channels of the first plurality of channels, and at least some channels of the second plurality of channels can include a second coating material on an interior surface of the at least some channels of the second plurality of channels.

Each member of the first plurality of channels can include an opening at the first surface and each member of the second plurality of channels can include an opening at an interface between the first and second layers, and wherein an average cross-sectional area of the openings of the first plurality of channels is different from an average cross-sectional area of the openings of the second plurality of channels. The average cross-sectional area of the openings of the first plurality of channels can be larger than the average cross-sectional area of the openings of the second plurality of channels. A ratio of a total area of the openings of the first plurality of channels at the first surface to an area of the first surface can be larger than a ratio of a total area of the openings of the second plurality of channels at the interface to an area of the interface.

Each member of the first plurality of channels can have a volume in the first layer and each member of the second plurality of channels can have a volume in the second layer, and a ratio of a total volume of the first plurality of channels in the first layer to a volume of the first layer can be larger than a ratio of a total volume of the second plurality of channels in the second layer to a volume of the second layer.

For each one of at least some members of the second plurality of channels, the member channel can have an opening with a first cross-sectional area at an interface between the first and second layers, and a second cross-sectional area at a location displaced from the interface along the member channel axis, and the first cross-sectional area can be smaller than the second cross-sectional area. A ratio of the first cross-sectional area to the second cross-sectional area can be 0.85 or less (e.g., 0.50 or less). Each member of the second plurality of channels can have an orientation relative to the first direction defined by a channel axis of the member, and a full width at half maximum (FWHM) of a distribution of the orientations of the second plurality of channels can be 20 degrees or less (e.g., 10 degrees or less).

Embodiments of the filters can also include any of the other features described herein, including any combinations of features individually described in connection with connection with different embodiments, except as expressly stated otherwise.

As used herein, the terms "about" means "approximately" (e.g., plus or minus 10% of the indicated value).

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described.

As used herein, the word "a" before a noun represents one or more of the particular noun. For example, the phrase "a mammalian cell" represents "one or more mammalian cells."

The terms "tangential flow filtration unit" or "TFF unit" are art-known and mean a device that includes at least one housing (such as a cylinder) and at least one cross-flow (tangential) filter positioned in the housing such that a large portion of the filter's surface is positioned parallel to the flow of a fluid (e.g., a cell culture) through the unit. TFF units are well-known in the art and are commercially available. The housing can include a first inlet/outlet and a second inlet/outlet positioned, e.g., to allow fluid to pass through the first inlet/outlet, cross the at least one cross-flow filter, and through the second inlet/outlet. In some examples, a circuit system can include multiple TFF units, e.g., connected in series and/or in parallel. For example, a circuit system that includes two or more TFF units can include fluid conduits fluidly connecting neighboring pairs of TFF units in the system. In other examples, a circuit system can include two or more sets of two or more TFF units fluidly connected by fluid conduits. Any of the TFF units described herein or known in the art are capable of receiving fluid in a first flow direction and a second flow direction.

The terms "tangential flow virus filtration unit" or "TFVF unit" are art-known and mean a device that includes at least one housing (such as a cylinder) and at least one cross-flow (tangential) virus filter positioned in the housing such that a large portion of the virus filter's surface is positioned parallel to the flow of a fluid (e.g., a cell culture) through the unit. The housing can include a first inlet/outlet and a second inlet/outlet positioned, e.g., to allow fluid to pass through the first inlet/outlet, cross the at least one cross-flow virus filter, and through the second inlet/outlet. In some examples, a circuit system can include multiple TFVF units, e.g., connected in series and/or in parallel. For example, a circuit system that includes two or more TFVF units can include fluid conduits fluidly connecting neighboring pairs of TFVF units in the system. In other examples, a circuit system can include two or more sets of two or more TFVF units fluidly connected by fluid conduits. Any of the TFVF units described herein or known in the art are capable of receiving fluid in a first flow direction and a second flow direction.

The term "cross-flow filter" or "tangential filter" is art known and means a filter that designed such that it can be positioned in a TFF or a TFVF unit such that a large portion of the filter's surface is parallel to the flow (e.g., first and second flow direction) of a fluid (e.g., a fluid including a recombinant therapeutic protein). For example, a cross-flow filter can have any shape that allows for tangential flow filtration, e.g., a tubular or rectangular shape. Particularly useful cross-flow filters are designed to result in a low amount of fluid turbulence or sheer stress in the fluid (e.g., cell culture) when the fluid is flowed (e.g., unidirectionally flowed to bidirectionally flowed) across the surface of the cross-flow filter. Cross-flow filters are commercially available, e.g., from Sartorius, MembraPure, Millipore, and Pall Corporation.

The term "low turbulence pump" or "LTP" is art-known and means a device that can move a fluid (e.g., a fluid including a recombinant therapeutic protein) within a system or circuit in a single direction (e.g., a first or second flow direction) or reversibly flowing a fluid (e.g., a fluid including a recombinant therapeutic protein) in two directions (a first and second flow direction) within the system without inducing a substantial amount of sheer stress or fluid turbulence in the fluid (e.g., a fluid including a recombinant therapeutic protein). When a LTP is used to flow a fluid (e.g., a fluid including a recombinant therapeutic protein) in alternating first and second flow directions, the second flow direction is approximately opposite to that of the first flow direction. An example of a LTP is a peristaltic pump. Other examples of LTPs are known in the art.

The term "mammalian cell" means any cell from or derived from any mammal (e.g., a human, a hamster, a mouse, a green monkey, a rat, a pig, a cow, or a rabbit). For example, a mammalian cell can be an immortalized cell. In some embodiments, the mammalian cell is a differentiated cell. In some embodiments, the mammalian cell is an undifferentiated cell. Non-limiting examples of mammalian cells are described herein. Additional examples of mammalian cells are known in the art.

The term "substantially free" means a composition (e.g., a liquid culture medium) that is at least or about 90% free (e.g., at least or about 95%, 96%, 97%, 98%, or at least or about 99% free, or about 100% free) of a specified substance (e.g., a mammalian cell).

The term "0.5× volume" means about 50% of the volume. The term "0.6× volume" means about 60% of the volume. Likewise, 0.7×, 0.8×, 0.9×, and 1.0× means about 70%, 80%, 90%, or 100% of the volume, respectively.

The term "culturing" or "cell culturing" means the maintenance or proliferation of a mammalian cell under a controlled set of physical conditions.

The term "culture of mammalian cells" means a liquid culture medium containing a plurality of mammalian cells that is maintained or proliferated under a controlled set of physical conditions.

The term "liquid culture medium" means a fluid that contains sufficient nutrients to allow a cell (e.g., a mammalian cell) to grow or proliferate in vitro. For example, a liquid culture medium can contain one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can contain serum from a mammal. In some embodiments, a liquid culture medium does not contain serum or another extract from a mammal (a defined liquid culture medium). In some embodiments, a liquid culture medium can contain trace metals, a mammalian growth hormone, and/or a mammalian growth factor. Another example of liquid culture medium is minimal medium (e.g., a medium containing only inorganic salts, a carbon source, and water). Non-limiting examples of liquid culture medium are described herein. Additional examples of liquid culture medium are known in the art and are commercially available. A liquid culture medium can contain any density of mammalian cells. For example, as used herein, a volume of liquid culture medium removed from a bioreactor can be substantially free of mammalian cells.

The term "animal-derived component free liquid culture medium" means a liquid culture medium that does not contain any components (e.g., proteins or serum) derived from a mammal.

The term "serum-free liquid culture medium" means a liquid culture medium that does not contain a mammalian serum.

The term "serum-containing liquid culture medium" means a liquid culture medium that contains a mammalian serum.

The term "chemically-defined liquid culture medium" is a term of art and means a liquid culture medium in which all of the chemical components are known. For example, a chemically-defined liquid culture medium does not contain fetal bovine serum, bovine serum albumin, or human serum albumin, as these preparations typically contain a complex mix of albumins and lipids.

The term "protein-free liquid culture medium" means a liquid culture medium that does not contain any protein (e.g., any detectable protein).

The term "agitation" means stirring or otherwise moving a portion of liquid culture medium in a bioreactor. This is performed in order to, e.g., increase the dissolved O2 concentration in the liquid culture medium in a bioreactor. Agitation can be performed using any art known method, e.g., an instrument or propeller. Exemplary devices and methods that can be used to perform agitation of a portion of the liquid culture medium in a bioreactor are known in the art.

The term "therapeutic protein drug substance" means a recombinant protein (e.g., an immunoglobulin, protein fragment, engineered protein, or enzyme) that has been sufficiently purified or isolated from contaminating proteins, lipids, and nucleic acids (e.g., contaminating proteins, lipids, and nucleic acids present in a liquid culture medium or from a host cell (e.g., from a mammalian, yeast, or bacterial host cell)) and biological contaminants (e.g., viral and bacterial contaminants), and can be formulated into a pharmaceutical agent without any further substantial purification and/or decontamination step.

The term "integrated process" means a process which is performed using structural elements that function cooperatively to achieve a specific result (e.g., the generation of a therapeutic protein drug substance from a liquid culture medium).

The term "continuous process" means a process which continuously feeds fluid through at least a part of the system. For example, in any of the exemplary continuous biological manufacturing systems described herein, a liquid culture medium containing a recombinant therapeutic protein is continuously fed into the system while it is in operation and a therapeutic protein drug substance is fed out of the system. In another example, a continuous process is a process which continuously feeds a liquid culture medium containing a recombinant therapeutic protein from a bioreactor through a first MCCS. Another example of a continuous process is a process which continuously feeds a liquid culture medium containing a recombinant therapeutic protein from a bioreactor through a first and second MCCS. Additional examples include a process which continuously feeds a liquid culture medium containing a recombinant therapeutic protein through a first MCCS, a process that continuously feeds a liquid culture medium containing a recombinant therapeutic protein through a first and second MCCS, or a process that continuously feeds a fluid containing a recombinant therapeutic protein through a second MCCS.

The term "immunoglobulin" means a polypeptide containing an amino acid sequence of at least 15 amino acids (e.g., at least 20, 30, 40, 50, 60, 70, 80, 90, or 100 amino acids) of an immunoglobulin protein (e.g., a variable domain sequence, a framework sequence, or a constant domain sequence). The immunoglobulin may, for example, include at least 15 amino acids of a light chain immunoglobulin, e.g., at least 15 amino acids of a heavy chain immunoglobulin. The immunoglobulin may be an isolated antibody (e.g., an IgG, IgE, IgD, IgA, or IgM). The immunoglobulin may be a subclass of IgG (e.g., IgG1, IgG2, IgG3, or IgG4). The immunoglobulin may be an antibody fragment, e.g., a Fab fragment, a F(ab')2 fragment, or an scFv fragment. The immunoglobulin may also be a bi-specific antibody or a tri-specific antibody, or a dimer, trimer, or multimer antibody, or a diabody, an Affibody®, or a Nanobody®. The immunoglobulin can also be an engineered protein containing at least one immunoglobulin domain (e.g., a fusion protein). Non-limiting examples of immunoglobulins are described herein and additional examples of immunoglobulins are known in the art.

The term "protein fragment" or "polypeptide fragment" means a portion of a polypeptide sequence that is at least or about 4 amino acids, at least or about 5 amino acids, at least or about 6 amino acids, at least or about 7 amino acids, at least or about 8 amino acids, at least or about 9 amino acids, at least or about 10 amino acids, at least or about 11 amino acids, at least or about 12 amino acids, at least or about 13 amino acids, at least or about 14 amino acids, at least or about 15 amino acids, at least or about 16 amino acids, at least or about 17 amino acids, at least or about 18 amino acids, at least or about 19 amino acids, or at least or about 20 amino acids in length, or more than 20 amino acids in length. A recombinant protein fragment can be produced using any of the processes described herein.

The term "engineered protein" means a polypeptide that is not naturally encoded by an endogenous nucleic acid present within an organism (e.g., a mammal). Examples of engineered proteins include enzymes (e.g., with one or more amino acid substitutions, deletions, insertions, or additions that result in an increase in stability and/or catalytic activity of the engineered enzyme), fusion proteins, antibodies (e.g., divalent antibodies, trivalent antibodies, or a diabody), and antigen-binding proteins that contain at least one recombinant scaffolding sequence.

The term "multi-column chromatography system" or "MCCS" means a system of a total of two or more interconnected or switching chromatography columns and/or chromatographic membranes. A non-limiting example of a multi-column chromatography system is a periodic counter current chromatography system (PCC) containing a total of two or more interconnected or switching chromatography columns and/or chromatographic membranes. Additional examples of multi-column chromatography systems are described herein and are known in the art.

The term "capturing" means a step performed to partially purify or isolate (e.g., at least or about 5%, e.g., at least or about 10%, 15%, 20%, 25%, 30%, 40%, 45%, 50%, 55%, 60%, 65%, 70%, 75%, 80%, 85%, 90%, or at least or about 95% pure by weight), concentrate, and stabilize a recombinant therapeutic protein from one or more other components present in a liquid culture medium or a diluted liquid culture medium (e.g., culture medium proteins or one or more other components (e.g., DNA, RNA, or other proteins) present in or secreted from a mammalian cell). Typically, capturing is performed using a resin that binds a recombinant therapeutic protein (e.g., through the use of affinity chromatography). Non-limiting methods for capturing a recombinant therapeutic protein from a liquid culture medium or diluted liquid culture medium are described herein and others are known in the art. A recombinant therapeutic protein can be captured from a liquid culture medium using at least one chromatography column and/or chromatographic membrane (e.g., any of the chromatography columns and/or chromatographic membranes described herein).

The term "purifying" means a step performed to isolate a recombinant therapeutic protein from one or more other impurities (e.g., bulk impurities) or components present in a fluid containing a recombinant therapeutic protein (e.g., liquid culture medium proteins or one or more other components (e.g., DNA, RNA, other proteins, endotoxins, viruses, etc.) present in or secreted from a mammalian cell). For example, purifying can be performed during or after an initial capturing step. Purification can be performed using a resin, membrane, or any other solid support that binds either a recombinant therapeutic protein or contaminants (e.g., through the use of affinity chromatography, hydrophobic interaction chromatography, anion or cation exchange chromatography, or molecular sieve chromatography). A recombinant therapeutic protein can be purified from a fluid containing the recombinant therapeutic protein using at least one chromatography column and/or chromatographic membrane (e.g., any of the chromatography columns or chromatographic membranes described herein).

The term "polishing" is a term of art and means a step performed to remove remaining trace or small amounts of contaminants or impurities from a fluid containing a recombinant therapeutic protein that is close to a final desired purity. For example, polishing can be performed by passing a fluid containing the recombinant therapeutic protein through a chromatographic column(s) or membrane absorber(s) that selectively binds to either the target recombinant therapeutic protein or small amounts of contaminants or impurities present in a fluid containing a recombinant therapeutic protein. In such an example, the eluate/filtrate of the chromatographic column(s) or membrane absorber(s) contains the recombinant therapeutic protein.

The term "eluate/filtrate" is a term of art and means a fluid that is emitted from a chromatography column or chromatographic membrane that contains a detectable amount of a recombinant therapeutic protein.

The term "filtering" means the removal of at least part of (e.g., at least 80%, 90%, 95%, 96%, 97%, 98%, or 99%) undesired biological contaminants (e.g., a mammalian cell, bacteria, yeast cells, viruses, or mycobacteria) and/or particulate matter (e.g., precipitated proteins) from a liquid (e.g., a liquid culture medium or fluid present in any of the systems or processes described herein).

The term "secreted protein" or "secreted recombinant protein" means a protein (e.g., a recombinant protein) that originally contained at least one secretion signal sequence when it is translated within a mammalian cell, and through, at least in part, enzymatic cleavage of the secretion signal sequence in the mammalian cell, is secreted at least partially into the extracellular space (e.g., a liquid culture medium). Skilled practitioners will appreciate that a "secreted" protein need not dissociate entirely from the cell to be considered a secreted protein.

The term "perfusion bioreactor" means a bioreactor containing a plurality of cells (e.g., mammalian cells) in a first liquid culture medium, wherein the culturing of the cells present in the bioreactor includes periodic or continuous removal of the first liquid culture medium and at the same time or shortly thereafter adding substantially the same volume of a second liquid culture medium to the bioreactor. In some examples, there is an incremental change (e.g., increase or decrease) in the volume of the first liquid culture medium removed and added over incremental periods (e.g., an about 24-hour period, a period of between about 1 minute and about 24-hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding).

The term "fed-batch bioreactor" is a term of art and means a bioreactor containing a plurality of cells (e.g., mammalian cells) in a first liquid culture medium, wherein the culturing of the cells present in the bioreactor includes the periodic or continuous addition of a second liquid culture medium to the first liquid culture medium without substantial or significant removal of the first liquid culture medium or second liquid culture medium from the cell culture. The second liquid culture medium can be the same as the first liquid culture medium. In some examples of fed-batch culture, the second liquid culture medium is a concentrated form of the first liquid culture medium. In some examples of fed-batch culture, the second liquid culture medium is added as a dry powder.

The term "clarified liquid culture medium" means a liquid culture medium obtained from a bacterial or yeast cell culture that is substantially free (e.g., at least 80%, 85%, 90%, 92%, 94%, 96%, 98%, or 99% free) of bacteria or yeast cells.

The term "unit operation" is a term of art and means a functional step that can be performed in a process of manufacturing a therapeutic protein drug substance from a liquid culture medium. For example, a unit of operation can be filtering (e.g., removal of contaminant bacteria, yeast viruses, or mycobacteria, and/or particular matter from a fluid containing a recombinant therapeutic protein), capturing, epitope tag removal, purifying, holding or storing, polishing, viral inactivating, adjusting the ionic concentration and/or pH of a fluid containing the recombinant therapeutic protein, and removing unwanted salts.

"Specific productivity rate" or "SPR" is a term of art and as used herein refers to the mass or enzymatic activity of a recombinant therapeutic protein produced per mammalian cell per day. The SPR for a recombinant therapeutic antibody is usually measured as mass/cell/day. The SPR for a recombinant therapeutic enzyme is usually measured as units/cell/day or (units/mass)/cell/day.

"Volume productivity rate" or "VPR" is a term of art and as used herein refers to the mass or enzymatic activity of recombinant therapeutic protein produced per volume of culture (e.g., per L of bioreactor, vessel, or tube volume) per day. The VPR for a recombinant therapeutic antibody is usually measured as mass/L/day. The VPR for a recombinant therapeutic enzyme is usually measured as units/L/day or mass/L/day.

Unless otherwise defined, all technical and scientific terms used herein have the same meaning as commonly understood by one of ordinary skilled in the art to which this invention belongs. Although methods and materials similar or equivalent to those described herein can be used in the practice of the present methods and systems, suitable methods and systems are described below. All publications, patent applications, patents, and other references mentioned herein are incorporated by reference in their entirety. In case of conflict, the present specification, including definitions, will control. In addition, the methods and examples are illustrative only and not intended to be limiting.

DESCRIPTION OF THE DRAWINGS

FIG. 8A is a schematic cross-sectional diagram of an example of a filter member.

FIG. 8B is a schematic cross-sectional diagram of another example of a filter member.

FIG. 10 is a schematic cross-sectional diagram of a further example of a filter member.

FIG. 11 is a schematic cross-sectional diagram of an example of a filter member with a channel that includes lateral projections.

Like reference symbols indicate like elements.

DETAILED DESCRIPTION

Introduction

Biomanufacturing systems hold tremendous promise for large-scale manufacture of a variety of different biological products, including therapeutic drug species such as recombinant protein substances. In many such systems, suitable cell cultures are combined with growth media, buffers and other input reagent streams in a bioreactor (e.g., a perfusion reactor) to generate product substances. Process fluids are extracted from the bioreactor and purified, typically via one or more multi-column chromatography purification units, to isolate desired products from the process fluids. Aspects of biomanufacturing systems and their related components are described, for example, in PCT Patent Application Publication No. WO 2018/035116, the entire contents of which are incorporated herein by reference.

Figure 1:
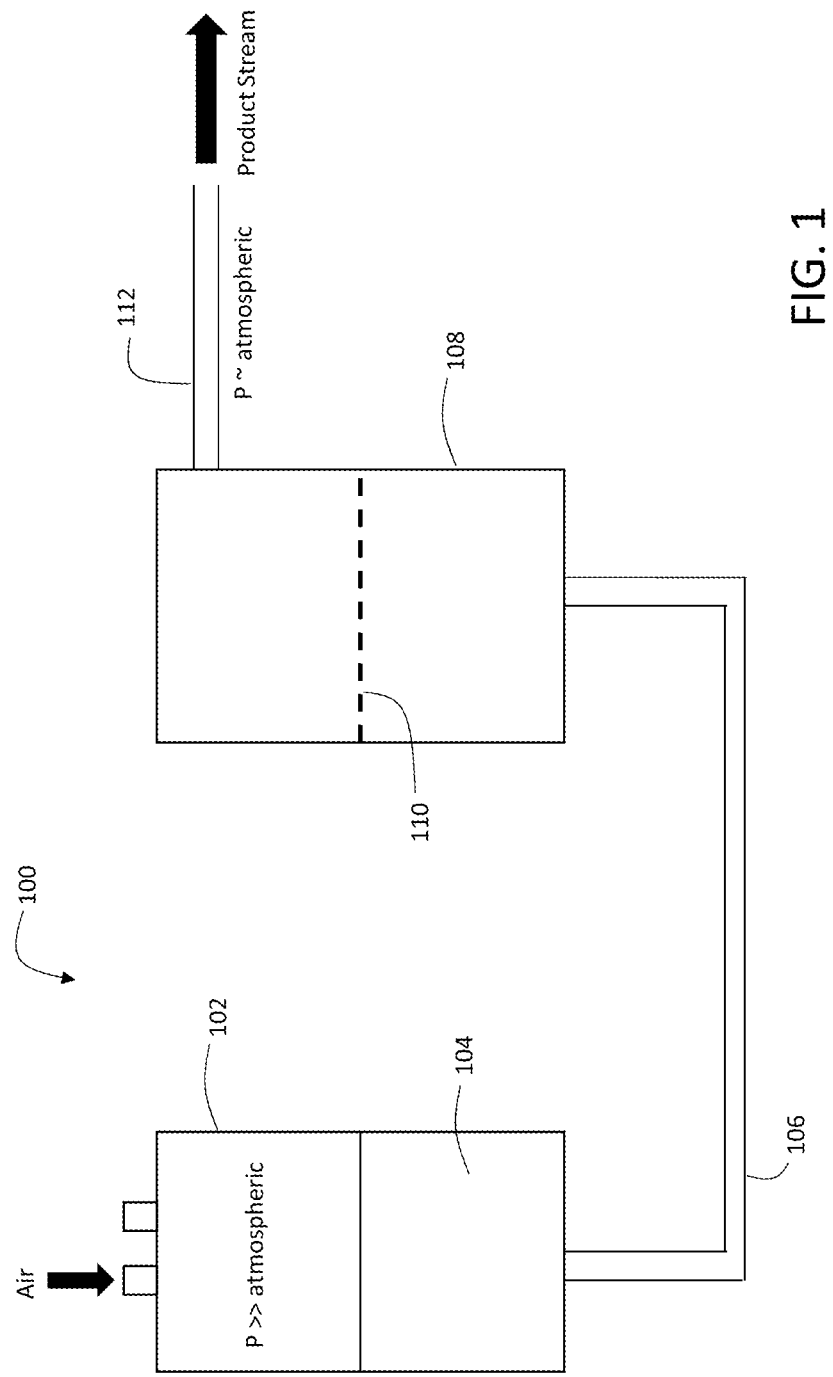
FIG. 1 is a schematic diagram of an example of a pressure-driven viral filtration sub-system.

Biomanufacturing systems also typically include a viral filtration stage or sub-system for removal of viral particles from a process fluid. Viral filtration sub-systems can generally be implemented in a variety of different configurations. For example, certain biomanufacturing systems include a pressure-driven viral filtration sub-system. FIG. 1 is a schematic diagram of a pressure-driven viral filtration sub-system 100. Sub-system 100 includes a feed vessel 102, a transport conduit 106, and a filter unit 108 with an internal filter membrane 110. During operation of sub-system 100, a fluid 104 (such as a process fluid extracted from a bioreactor or from another component of a biomanufacturing system downstream from a bioreactor) is introduced into feed vessel 102, either continuously or in batches. Feed vessel 102 is pressurized so that the gas pressure within feed vessel 102 is significantly larger than atmospheric pressure, creating a pressure gradient relative to an outlet of the sub-system that drives the flow of fluid 104 out of feed vessel 102 through conduit 106 and into filter unit 108. Once within filter unit 108, fluid 104 passes through filter member 110, which filters out viral particles.

The flow of fluid 104 in sub-system 100 is entirely pressure-driven, with a single parameter (the feed vessel gas pressure) determining the flux through filter unit 108. A pressure drop occurs only across filter member 110, as the gas pressure on the downstream side of filter member 110 containing the product stream 112 is effectively atmospheric pressure. Product stream 112 corresponds to fluid 104 with viral particles removed.

It should be noted that in sub-system 100, viral particles, or other process impurities (such as host cell proteins, sub-visible particles, or the protein product itself), accumulate in filter member 110. Accordingly, the useful lifetime of filter member 110 is limited by the elapsed time before viral breakthrough or filter clogging occurs, and viral particles in fluid 104 on the upstream side of filter member 110 are not fully trapped by filter member 110 (i.e., a certain number of particles pass through filter member 110 and emerge in product stream 112). Thus, while sub-system 100 can be implemented in a fairly simple configuration and provides effective filtration of viral particles, filter member 110 can be prone to fouling during operation, which can limit the effectiveness of this type of viral filtration and increase its cost. Because of the relatively short operating window before filter member 110 is changed, sub-system 100 can be better suited to batch operations than to continuous viral filtration operations as part of a continuous biomanufacturing process.

Figure 2:
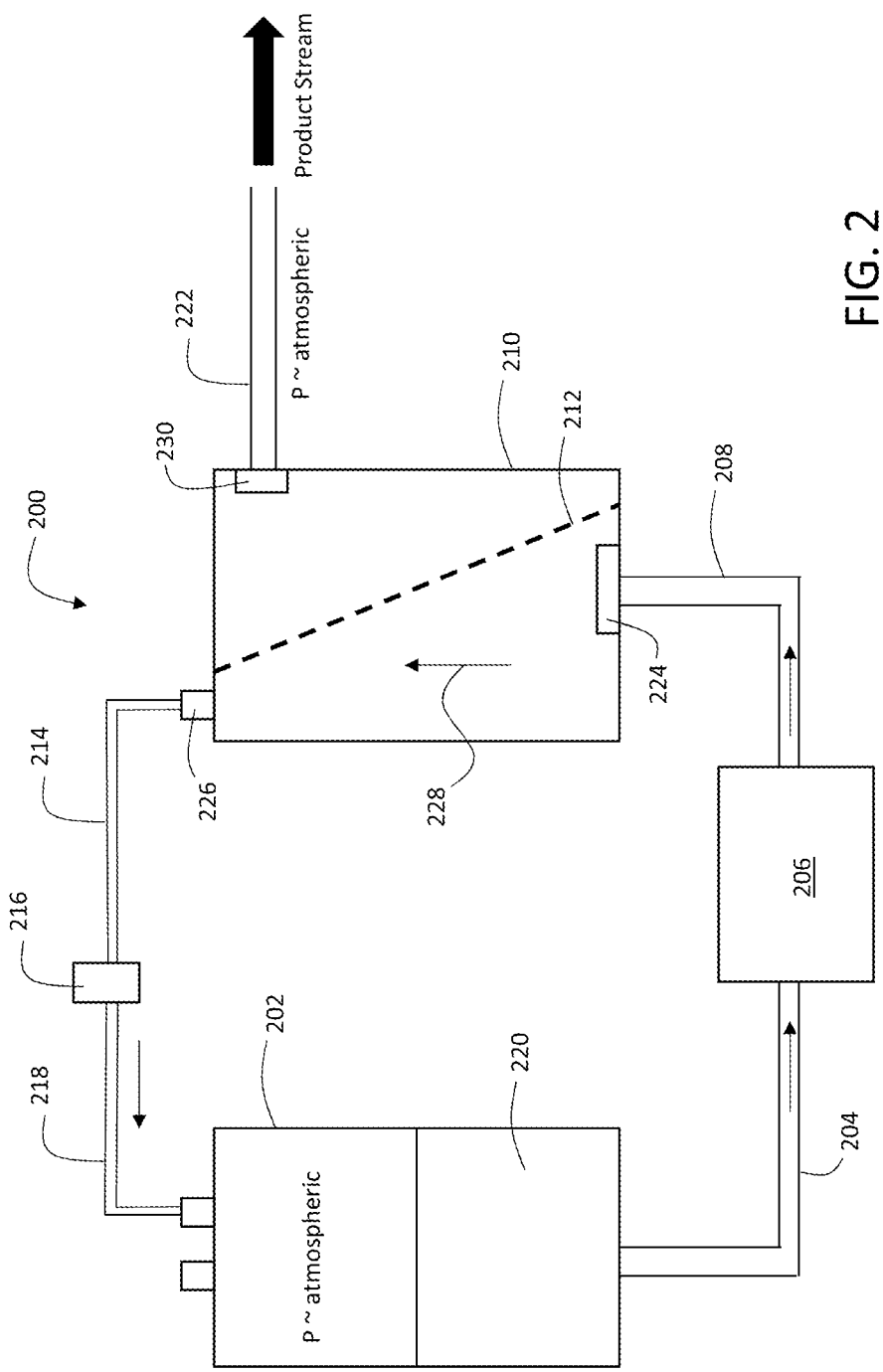
FIG. 2 is a schematic diagram of an example of a tangential flow viral filtration sub-system.

FIG. 2 is a schematic diagram of a tangential flow filtration sub-system 200. Sub-system 200 includes a feed vessel 202 that retains a fluid 220 (e.g., a process fluid containing one or more products from a bioreactor). Sub-system 200 is pump-driven, and includes a pump 206. During operation, pump 206 drives fluid 220 from feed vessel 202 through conduits 204 and 208 and into filter unit 210, which includes a filter member 212. Filter member 212 is typically a planar membrane, for example, and is oriented approximately tangentially to a flow direction of fluid 220 within filter unit 210. Specifically, within filter unit 210, fluid 220 flows from an inlet 224 to an outlet 226, in a direction approximately along the length of filter unit 210, as indicated by arrow 228. As fluid actively flows in direction 228, a portion of the fluid moves tangentially through member 212, in the direction of outlet 230. The tangentially moving fluid is filtered by member 212 to remove viral particles, so that the product stream 222 emerging from outlet 230 does not contain viral particles. Fluid 220 that does not move through filter member 212 leaves filter unit 210 through outlet 226 as retentate, and is recirculated through conduits 214 and 218 back into feed vessel 202. A flow control device 216 can be used to regulate the retentate pressure.

In effect, two process variables control the rate at which a filtered product stream is generated in sub-system 200: the flow rate of fluid 220, controlled by pump 206, and the retentate pressure, controlled by flow control device 216. Pressure drops occur at multiple locations in sub-system 200 (i.e., between inlet 224 and outlets 230 and 226, and between outlet 226 and feed vessel 202.

Tangential flow viral filtration (TFVF) sub-systems have a number of advantages relative to conventional "dead-end" filtration systems, such as in FIG. 1. In TFVF, a flux of fluid 220 is maintained across member 212 via a "sweeping" flow motion of fluid 220, which can yield a higher throughput per unit area of the filter membrane. TFVF sub-systems are therefore better suited for implementation in continuous biomanufacturing systems, as they can accommodate continuous inflows of process fluids from bioreactors and generate continuous outflows of product streams for further purification and/or analysis. TFVF sub-systems can also be implemented in batch biomanufacturing systems to increase the lifetime of a viral filtration membrane due to the relatively lower amount of filter fouling accorded by the tangential mode of operation. Limitations to TFVF sub-systems can sometimes include a generally narrower available set of filter members, and the use of a recirculation pump, which can impose certain operating constraints on the sub-system.

Figure 3:
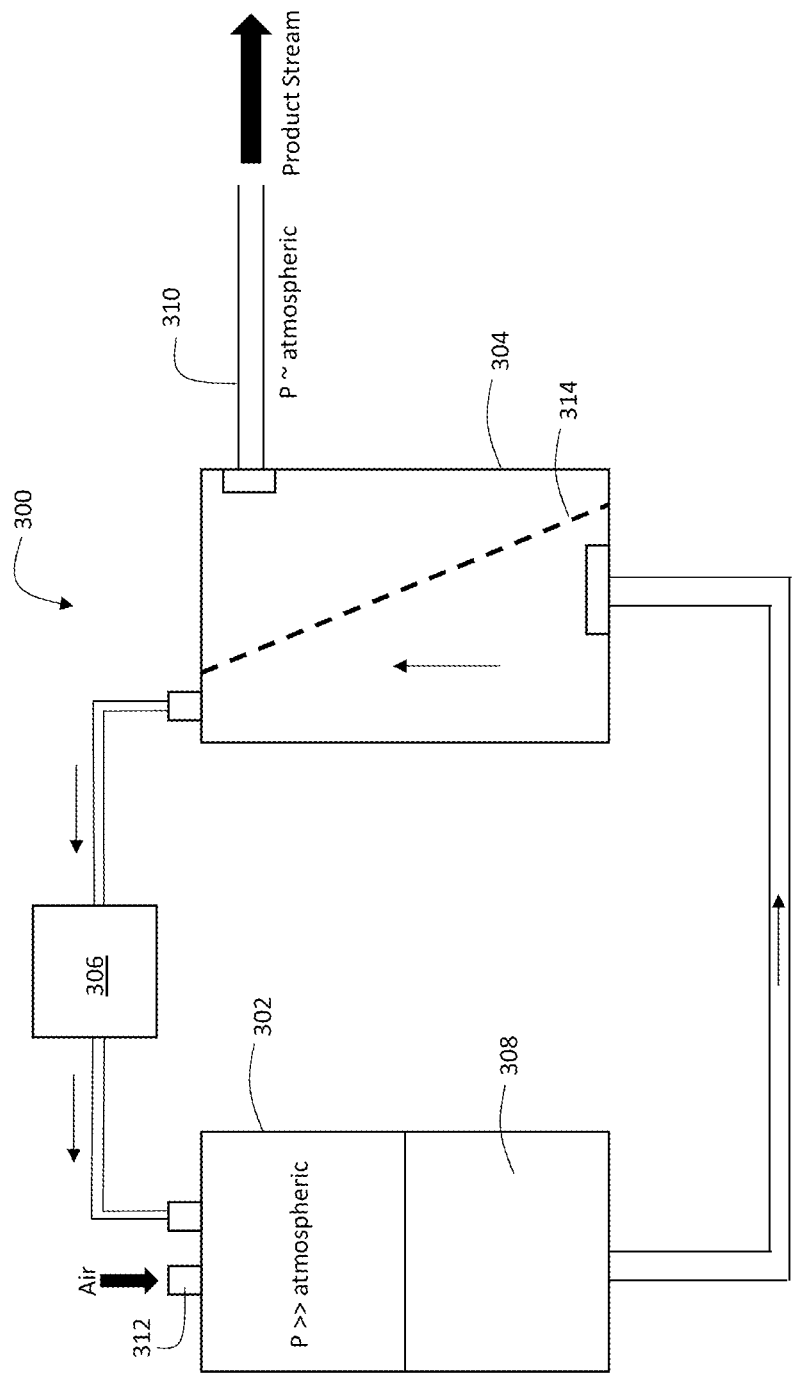
FIG. 3 is a schematic diagram of an example of a tangential flow viral filtration sub-system that is both pressure- and pump-driven.

It is possible to implement a TFVF sub-system that is both pressure- and pump-driven. FIG. 3 is a schematic diagram of such a sub-system 300, which includes a feed vessel 302, a filter unit 304, and a recirculating pump 306. These components function in a manner similar to the corresponding components of FIG. 2 above. During operation, feed vessel 302 is pressurized by delivery of air or another gas through inlet 312. Fluid 308 flows from feed vessel 302 to filter unit 304, which includes a tangentially oriented filter member 314. As fluid 308 flows across member 314, a portion of the fluid moves through membrane 314, which removes viral particles from the fluid so that the product stream 310 that emerges from filter unit 304 is free of viral particles. The fluid that does not diffuse through filter member 314 emerges from filter unit 304 as retentate, and is recirculated by pump 306 back into feed vessel 302. Thus, in sub-system 300, both the pressurized feed vessel 302 and pump 306 drive the circulation of fluid 308 through the sub-system.

As above, two operating parameters can be adjusted to control the circulation of fluid 308 through sub-system 300: the recirculation flow rate (determined by pump 306) and the system fluid pressure (via the pressurization of feed vessel 302). One advantage of sub-system 300 is that in the re-circulating portion of the sub-system, the fluid pressure remains effectively constant. That is, the fluid pressure in the feed vessel 302, at the entrance of filter member 314, and of the retentate emerging from filter member 314 is approximately the same. In sub-system 300, the only significant pressure drop occurs across filter member 314. As a result, the rate at which the product stream emerges from filter member 314 is relatively straightforward to control.

Figure 4:
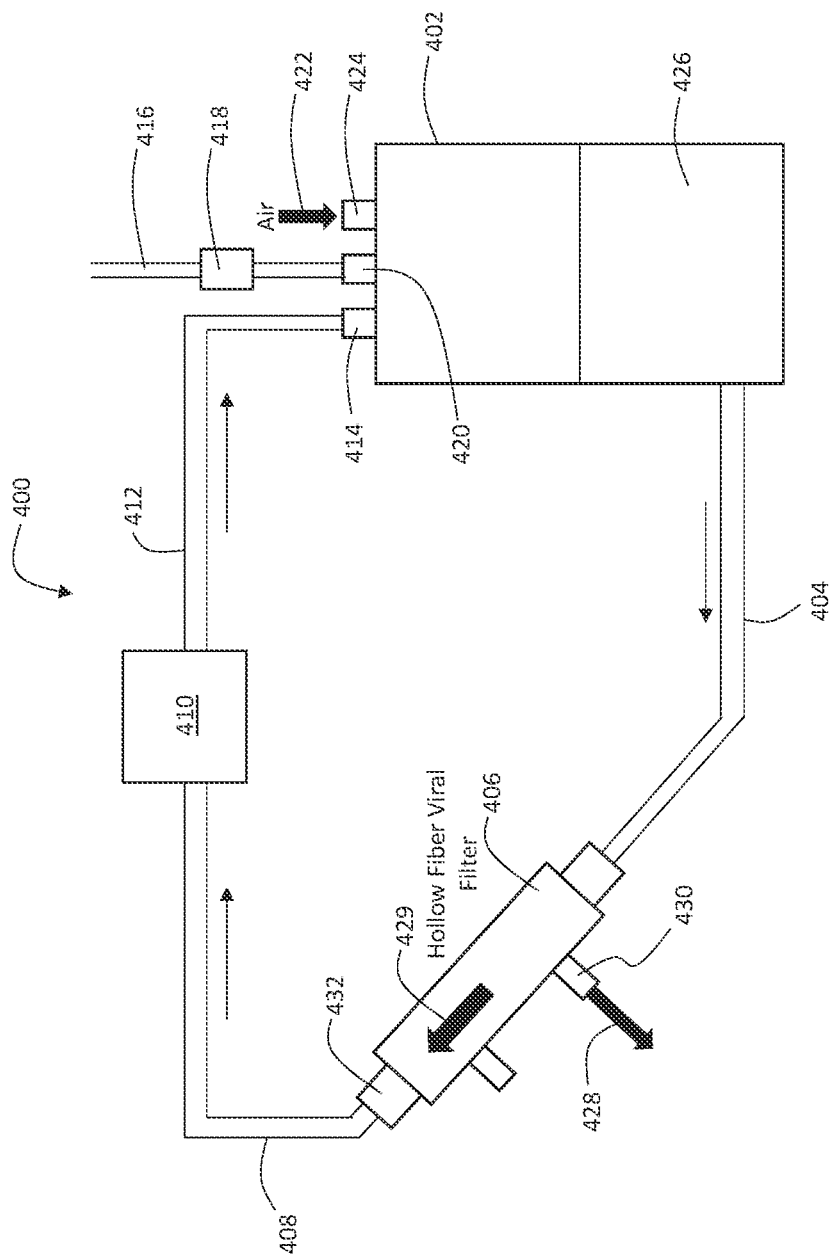
FIG. 4 is a schematic diagram of an example of a constant pressure, constant tangential flow viral filtration sub-system.

Sub-system 300 is one example of a constant pressure system. By adjusting pump 306 appropriately, sub-system 300 can also be operated at a constant tangential flow rate, ensuring that a continuous product stream 310 emerges from filter unit 304 at a constant rate. Constant-pressure, constant tangential flow filtration sub-systems can also be implemented in different ways. FIG. 4 is a schematic diagram showing another example of a filtration sub-system 400 that includes a feed vessel 402, a conduit 404 connected between feed vessel 402 and a filter unit 406, a conduit 408 connected between filter unit 406 and a pump 410, and a conduit 412 connected between pump 410 and an inlet 414 of feed vessel 402.

During operation of sub-system 400, air or another gas is delivered through inlet 424 to feed vessel 402, pressurizing the interior of the feed vessel. The fluid pressure within feed vessel 402 drives transport of a fluid 426 (e.g., a process fluid derived from a bioreactor, or from an intermediate purification stage of a biomanufacturing system) present in feed vessel out of the feed vessel through conduit 404 and into filter unit 406. Filter unit 406 includes a filter member (not shown in FIG. 4) that is oriented such that the fluid 426 within filter unit 406 flows in a direction indicated by arrow 429 that is tangent to (or approximately tangent to) a surface of the filter member. A portion of the fluid 426 moves through the filter member in a direction orthogonal to arrow 429 (i.e., in a radial direction) and emerges from filter unit 406 through outlet 430 as product stream 428, with little or no viral load. The remaining fluid 426 emerges from filter unit 406 through outlet 432 as a retentate and circulates through pump 410 via conduits 408 and 412. Pump 410 drives the flow of the retentate back into feed vessel 402 through inlet 414. As a result, sub-system 400 is capable of continuously filtering fluid 426, with a portion of fluid 426 being removed from the sub-system as a filtered product stream 428, and the remaining fluid 426 recirculating for another pass through filter unit 406. Additional fluid 426 can be introduced into sub-system 400 prior to or during operation, via conduit 416 and one-way valve 418; the additional fluid 426 is introduced into feed vessel 402 through inlet 420.

Figure 5:
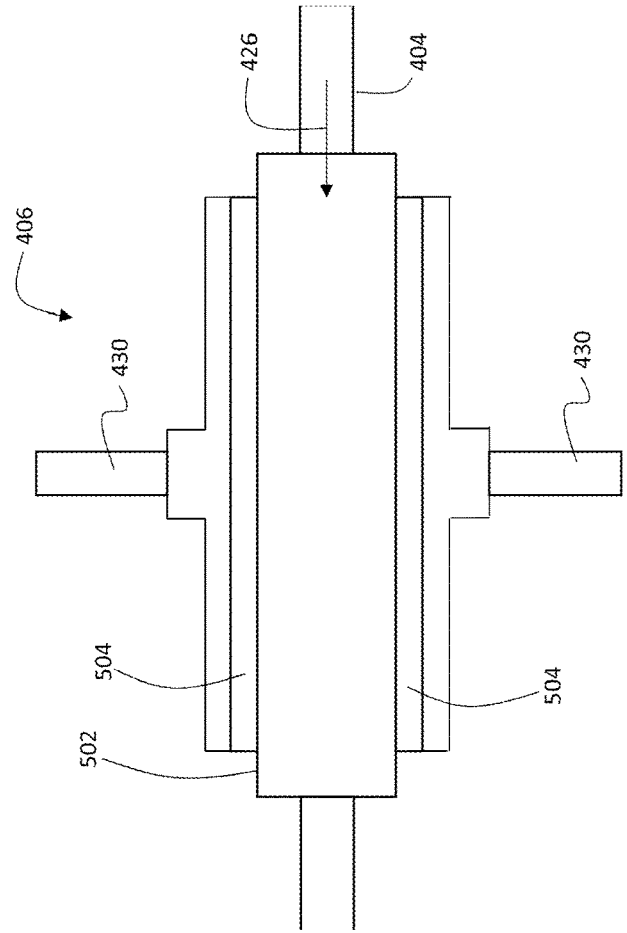
FIG. 5 is a schematic diagram of an example of a filter member.

The structure of filter unit 406 and the filter member therein differs from the corresponding filter unit in FIG. 3. In FIG. 4, filter unit 406 includes a hollow fiber-based filter member. FIG. 5 is a schematic cross-sectional diagram showing an example of filter member 406. Filter unit 406 includes a filter body 502, a filter member 504, and outlets 430. Conduits 404 and 408 are connected to an interior channel within filter body 502. As is evident from FIG. 5, filter body 502 is formed from a hollow fiber, with apertures formed in the sidewalls of the fiber. Filter member 504 contacts the sidewalls of the fiber, and effectively has a tube-shaped structure. Fluid 426 enters filter body 520 and flows in the direction shown by the arrow in FIG. 5. A portion of fluid 426 passes through filter member 504 and emerges from outlet 430 as a product stream. The remaining fluid 426 emerges into conduit 408 as retentate and is recirculated by a pump (e.g., pump 410).

In a dead-end filter unit (as shown for example in FIG. 1), fluid pressure within the filter unit—which drives the flow of fluid through the filter—also compresses solid material against the front surface of the filter, which leads to a reduction in throughput as the open volume within the filter member is reduced. For fluids with significant suspended solid matter, fouling of the filter member can occur relatively quickly.

Filter unit 406 has a number of advantages compared with such dead-end filter units. Because fluid 426 flows in a tangential direction relative to the sidewalls of filter body 502 and filter member 504, the crossflow of fluid 426 helps to "sweep away" solid particles from the surface of filter member 504, which helps to reduce the rate of fouling of the filter member surface.

Further, both the flow rate of fluid 426 across the surface of filter member 504 (which is referred to as the "crossflow rate") and the fluid pressure within filter member 504 can be regulated by adjusting pump 410 and the pressure within feed vessel 402, respectively. As fluid 426 flows through filter member 504 and filter body 502, a transmembrane pressure (TMP) is applied across the thickness of filter member 504. The TMP can be adjusted by changing the crossflow rate (e.g., via pump 410) and/or by changing the fluid pressure in vessel 402. The TMP pressure drives a portion of fluid 426 to pass through filter member 504, filtering out viral particles from the fluid and generating product stream 428. Due to the crossflow sweeping action of fluid 426 and the adjustability of the crossflow rate and TMP, filter unit 406 can typically operate for significantly longer periods of time before fouling occurs and replacement is required, relative to comparable dead-end filter units.

Typically, viral filter members are not used in tangential flow filtration systems, but are instead used in dead-end filtration systems such as in FIG. 1. For viral filtration in dead-end systems, viral filter members are typically relatively thin to ensure high flow rates (e.g., high flux) of fluid through the filter members. As discussed above, such viral filter members tend to foul relatively rapidly, and are therefore not well suited for continuous filtration operations over periods of days or weeks.

Continuous Viral Filtration

To perform viral filtration on a continuous basis for process fluids extracted directly from bioreactors or from intermediate purification stages of a biomanufacturing system, the inventors have implemented a tangential flow viral filtration sub-system as shown in FIGS. 4 and 5. Further, the inventors have discovered that such sub-systems—and in particular, the viral filter member—can be configured in various ways to reduce the rate at which the filter member fouls, allowing extended periods of continuous operation.

In some embodiments, the tangential flow viral filtration sub-system is configured such that the lateral fluid pressure applied to the filter member (i.e., the transmembrane pressure) is between 0 psi and 50 psi (e.g., between 0 psi and 45 psi, between 0 psi and 40 psi, between 0 psi and 35 psi, between 0 psi and 30 psi, between 0 psi and 25 psi, between 0 psi and 20 psi, between 0 psi and 15 psi, between 0 psi and 10 psi, between 5 psi and 50 psi, between 5 psi and 40 psi, between 5 psi and 30 psi, between 5 psi and 20 psi, between 10 psi and 50 psi, between 10 psi and 40 psi, between 10 psi and 30 psi, between 10 psi and 20 psi, between 15 psi and 50 psi, between 15 psi and 40 psi, between 15 psi and 30 psi, between 20 psi and 50 psi, between 20 psi and 40 psi, between 25 psi and 50 psi, or any range of pressures between 0 psi and 50 psi). In certain embodiments, the lateral fluid pressure applied to the filter member is 50 psi or less (e.g., 45 psi or less, 40 psi or less, 35 psi or less, 30 psi or less, 25 psi or less, 20 psi or less, 15 psi or less, 10 psi or less, 5 psi or less, 4 psi or less, 3 psi or less, 2 psi or less, 1 psi or less, 0.5 psi or less, 0.25 psi or less, or even less).

In general, by selecting a lower lateral fluid pressure, the flux across the filter member is reduced, which reduces the rate at which the product stream is generated. However, it has been observed by the inventors that a lower later fluid pressure increases the useful lifetime of the viral filter member by increasing the elapsed time before viral breakthrough at the outer surface of the filter member.

Figure 6:
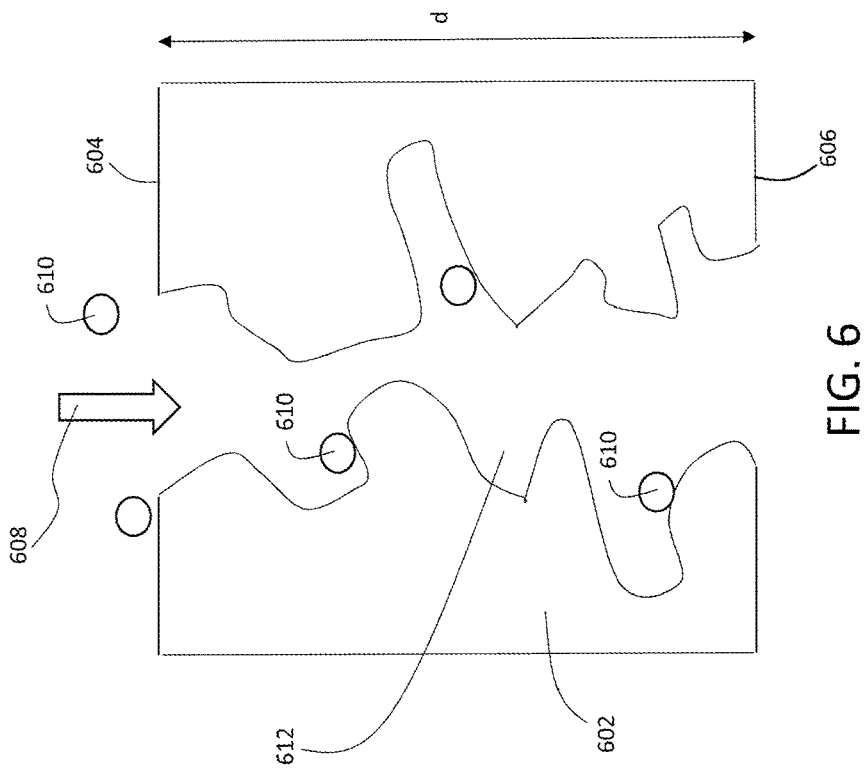
FIG. 6 is a schematic cross-sectional diagram of a filter member.

FIG. 6 is a schematic cross-sectional diagram of a viral filter member 602. Filter member 602 includes a first surface 604 and a second surface 606. Multiple channels 612 extend through the filter member from the first surface 604 to the second surface 606. A fluid 608 that includes viral particles 610 encounters the first surface 604 of the filter member, and flows from first surface 604 to second surface 606 through channels 612. As fluid 608 flows through channels 612, viral particles 610 adsorb onto the channel walls, where they are retained, so that prior to fouling of the filter member, the product stream that emerges from second surface 606 is substantially free of viral particles.

Without wishing to be bound by theory, it is believed that once viral particles are within channels 612, fluid transport carries the viral particles toward the second surface 606. Moreover, even adsorbed viral particles can desorb and propagate by Brownian motion or fluid transport toward second surface 606. By reducing the lateral fluid pressure applied to the filter member, the fluid flow rate through the membrane is reduced, thereby reducing the rate at which viral particles are transported toward second surface 606, and extending the lifetime of the filter member before viral breakthrough at the second surface occurs.

In some embodiments, the thickness of the filter member (shown in FIG. 6 as "d", between the first and second surfaces of the filter member) is considerably larger than the thickness of standard tangential filter membranes. For example, conventional filter membranes for use in tangential filtration operations range in thickness from about 20 microns to 140 microns. The filter member 602 used in the tangential flow viral filtration sub-systems described herein can have a thickness d of 150 microns or more (e.g., 160 microns or more, 170 microns or more, 180 microns or more, 190 microns or more, 200 microns or more, 220 microns or more, 240 microns or more, 260 microns or more, 280 microns or more, 300 microns or more, 320 microns or more, 340 microns or more, 350 microns or more, 370 microns or more, 400 microns or more, 450 microns or more, or even more).

In certain embodiments, the thickness of the filter member between the first and second surfaces varies. For example, a minimum thickness of the filter member between the surfaces can be 50 microns or more (e.g., 60 microns or more, 70 microns or more, 80 microns or more, 90 microns or more, 100 microns or more, 110 microns or more, 120 microns or more, 130 microns or more, 140 microns or more, 150 microns or more, 160 microns or more, 170 microns or more, 180 microns or more, 190 microns or more, 200 microns or more), and a maximum thickness of the filter member between the surfaces can be 1000 microns or less (e.g., 900 microns or less, 800 microns or less, 700 microns or less, 600 microns or less, 500 microns or less, 475 microns or less, 450 microns or less, 425 microns or less 400 microns or less, 375 microns or less, 350 microns or less, 325 microns or less, 300 microns or less, or even less).

Figure 7C:
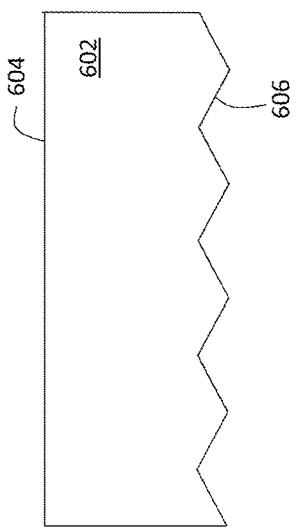
FIGS. 7A-7E are schematic diagrams of examples of filter members of varying thickness between first and second surfaces.
Figure 7B:
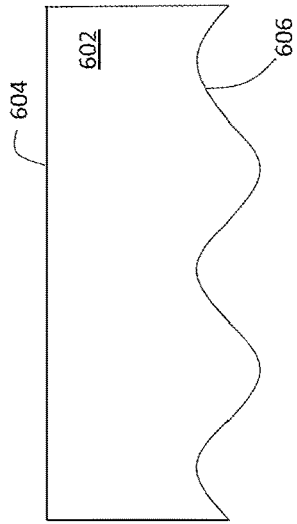
Figure 7A:
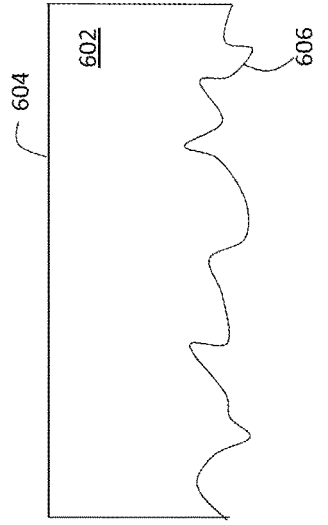
Figure 7E:
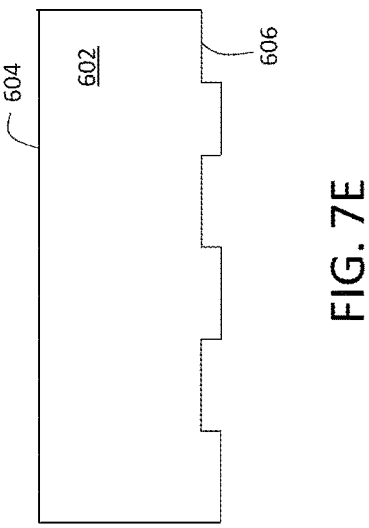
Figure 7D:
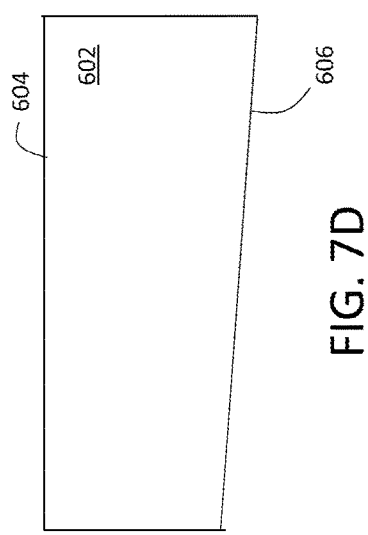

The thickness of the filter member between the first and second surfaces can vary in a random manner, or in regular fashion. FIGS. 7A-7E are schematic diagrams showing examples of filter members 602 with varying thicknesses between first surface 604 and second surface 606. In FIG. 7A, the thickness of the filter member varies irregularly along the length of the member. In FIG. 7B, the thickness of the filter member varies regularly, with second surface 606 having an undulating, oscillatory, or sinusoidal pattern of peaks and valleys. In FIG. 7C, the thickness of the filter member varies regularly, with second surface having a sawtooth shape, forming a pattern of peaks and valleys with the thickness of the member varying linearly between the peaks and valleys. In FIG. 7D, the thickness of the filter member varies monotonically along the length of the member. The thickness can vary linearly or non-linearly along the length of the member. In FIG. 7E, the thickness of the filter member varies in stepped fashion.

In general, during tangential viral filtering operations, the flow rate of the fluid through the filter member is selected to ensure that the product stream flux is sufficiently high to maintain continuous manufacturing operation, while at the same time low enough to ensure that viral particles do not break through the filter member and emerge in the product stream. For example, per unit area of the filter member, the flow rate can be at least 0.5 $L/m^2/hr.$ (e.g., at least 1.0 $L/m^2/hr.$, at least 2.0 $L/m^2/hr.$, at least 5.0 $L/m^2/hr.$, at least 10.0 $L/m^2/hr.$, at least 15.0 $L/m^2/hr.$, at least 20.0 $L/m^2/hr.$, at least 30.0 $L/m^2/hr.$, at least 40.0 $L/m^2/hr.$) The flow rate can also, or alternatively, be 100 $L/m^2/hr.$ or less (e.g., 90 $L/m^2/hr.$ or less, 80 $L/m^2/hr.$ or less, 70 $L/m^2/hr.$ or less, 60 $L/m^2/hr.$ or less).

The bulk porosity of the filter member is generally chosen to balance the flow rate of fluid through the member, the viral particle retention capacity of the member, and the mechanical strength of the member. In some embodiments, the porosity of the filter member (i.e., the pore volume fraction of the filter member) is 0.05 or more, (e.g., 0.10 or more, 0.15 or more, 0.20 or more, 0.25 or more, 0.30 or more, 0.35 or more, 0.40 or more, 0.45 or more, 0.50 or more, 0.55 or more, 0.60 or more, or even more). In certain embodiments, the porosity of the filter member is 0.90 or less (e.g., 0.88 or less, 0.86 or less, 0.84 or less, 0.82 or less, 0.80 or less, 0.78 or less, 0.76 or less, 0.74 or less, 0.72 or less, 0.70 or less, or even less). The porosity of the filter member can be, for example, between 0.30 and 0.90, or any smaller range within this range.

In some embodiments, the thickness of the filter member may be small relative to the lateral dimensions of the filter member. For example, the filter member can have a maximum lateral dimension when extended in a plane, and a ratio of the maximum lateral dimension of the filter member to the thickness of the filter member can be 5 or more (e.g., 10 or more, 15 or more, 20 or more, 30 or more, 40 or more, 50 or more, 75 or more, 100 or more).

Filter members can generally be formed from a wide variety of materials. Examples of suitable materials include, but are not limited to, polyvinylidene difluoride (PVDF), hydrophilized PVDF, regenerated cellulose, and other materials used to construct chemical synthetic membranes. Filter fabrication methods generally known in the art can be used and/or modified to fabricate the filter members described herein.

Channel Architecture

The filter member includes pores or channels that extend between the first and second surfaces of the member, and permit fluid to pass through the filter member. At the same time, viral particles are trapped within the pores (e.g., by adsorption), and thereby prevented from emerging in the product stream. The following discussion will refer to "channels" in the filter member, but it should be understood that the term "pores" could also be used to describe the same features.

FIG. 8A is a schematic cross-sectional diagram of a filter member 602 that includes channels 802. The number density of channels per unit on the first surface 604 of filter member 602 can be, for example, between 100/cm$^2$ and 10,000/cm$^2$. That is, the number density of channels can be 100/cm$^2$ or more (e.g., 200/cm$^2$ or more, 300/cm$^2$ or more, 400/cm$^2$ or more, 500/cm$^2$ or more, 600/cm$^2$ or more, 700/cm$^2$ or more, 800/cm$^2$ or more, 900/cm$^2$ or more, 1000/cm$^2$ or more, 1500/cm$^2$ or more, 2000/cm$^2$ or more, 2500/cm$^2$ or more, 3000/cm$^2$ or more, 3500/cm$^2$ or more, 4000/cm$^2$ or more, 4500/cm$^2$ or more, or even more). The number density of channels can be 10,000/cm$^2$ or less (e.g., 9500/cm$^2$ or less, 9000/cm$^2$ or less, 8500/cm$^2$ or less, 8000/cm$^2$ or less, 7500/cm$^2$ or less, 7000/cm$^2$ or less, 6500/cm$^2$ or less, 6000/cm$^2$ or less, 5500/cm$^2$ or less, or even less).

In some embodiments, the opening sizes of one or more of the channels formed in filter member 602 in the first and second surfaces 604 and 606 are approximately the same (i.e., the cross-sectional areas of the openings in the surfaces are the same within 10%). In certain embodiments, however, the opening sizes differ. In particular, filter member 602 can be fabricated so that for individual channels, the cross-sectional area of the channel opening in the first surface 604 is larger than the cross-sectional area of the channel opening in the second surface, such that the effective diameter of the channel narrows through the body of the filter member. It has been discovered that by using such tapered channels, breakthrough of viral particles at the second surface 606 is impeded. Without wishing to be bound by theory, it is believed that this is due to the smaller channel opening, and also due to the reduced flow rate of the fluid through the channel.

FIG. 8B is a schematic diagram of a filter member 602 that includes a plurality of tapered channels 808 (only one channel is shown in FIG. 8B for clarity). The opening 806 of channel 804 at the first surface 604 of the filter member has a larger cross sectional area than the opening of channel 804 at the second surface 606 of the filter member. The cross-sectional area of opening 806, $A_1$, can generally be between 0.1 μm$^2$ and 10 μm$^2$. For example, the cross-sectional area can be 0.1 μm$^2$ or more (e.g., 0.2 μm$^2$ or more, 0.3 μm$^2$ or more, 0.4 μm$^2$ or more, 0.5 μm$^2$ or more, 0.6 μm$^2$ or more, 0.7 μm$^2$ or more, 0.8 μm$^2$ or more, 0.9 μm$^2$ or more, 1.0 μm$^2$ or more, 2.0 μm$^2$ or more, 3.0 μm$^2$ or more, 4.0 μm$^2$ or more, 5.0 μm$^2$ or more, or even more). Alternatively or in addition, the cross-sectional area can be 10 μm$^2$ or less (e.g., 9.5 μm$^2$ or less, 9.0 μm$^2$ or less, 8.5 μm$^2$ or less, 8.0 μm$^2$ or less, 7.5 μm$^2$ or less, 7.0 μm$^2$ or less, 6.5 μm$^2$ or less, 6.0 μm$^2$ or less, or even less).

The cross-sectional area of opening 808 of channel 804 is $A_2$. In general, the ratio $A_2/A_1$ can be 1.0 or less (e.g., 0.95 or less, 0.90 or less, 0.85 or less, 0.80 or less, 0.75 or less, 0.70 or less, 0.65 or less, 0.60 or less, 0.55 or less, 0.50 or less, 0.45 or less, 0.40 or less, 0.35 or less, 0.30 or less, or even less). Among the multiple channels in filter member 602, any of the channels can have cross-sectional areas $A_1$ and $A_2$ as discussed above. Moreover, within a single filter member, the cross-sectional areas $A_1$ and/or $A_2$ of the multiple channels can be the same, or the cross-sectional areas $A_1$ and/or $A_2$ can be different.

For a filter member 602 having a plurality of channels 804, the channels may have a distribution of cross-sectional areas $A_1$. A mean value of the distribution of cross-sectional areas $A_1$ can be between 0.1 μm$^2$ and 10 μm$^2$. For example, the mean value of the cross-sectional area can be 0.1 μm$^2$ or more (e.g., 0.2 μm$^2$ or more, 0.3 μm$^2$ or more, 0.4 μm$^2$ or more, 0.5 μm$^2$ or more, 0.6 μm$^2$ or more, 0.7 μm$^2$ or more, 0.8 μm$^2$ or more, 0.9 μm$^2$ or more, 1.0 μm$^2$ or more, 2.0 μm$^2$ or more, 3.0 μm$^2$ or more, 4.0 μm$^2$ or more, 5.0 μm$^2$ or more, or even more). Alternatively or in addition, the mean value of the cross-sectional area can be 10μ$^2$ or less (e.g., 9.5 μm$^2$ or less, 9.0 μm$^2$ or less, 8.5 μm$^2$ or less, 8.0 μm$^2$ or less, 7.5 μm$^2$ or less, 7.0 μm$^2$ or less, 6.5 μm$^2$ or less, 6.0μ$^2$ or less, or even less).

A full-width at half-maximum (FWHM) value of the distribution of cross-sectional areas $A_1$ can be between 0.05 μm$^2$ and 5.0 μm$^2$. For example, the FWHM value of the distribution can be 0.05 μm$^2$ or more (0.1 μm$^2$ or more, 0.2 μm$^2$ or more, 0.3 μm$^2$ or more, 0.5 μm$^2$ or more, 1.0 μm$^2$ or more, 2.0 μm$^2$ or more, or even more) and/or 5.0 μm$^2$ or less (e.g., 4.5 μm$^2$ or less, 4.0 μm$^2$ or less, 3.5 μm$^2$ or less, 3.0 μm$^2$ or less, or even less).

The opening 806 of each channel 804 in first surface 604 has a minimum opening dimension corresponding to the shortest distance spanning the opening and passing through the center of mass of the opening. For each opening 806, the minimum opening dimension can be 20 nm or more (e.g., 25 nm or more, 30 nm or more, 35 nm or more, 40 nm or more, 45 nm or more, 50 nm or more, 60 nm or more, 70 nm or more, 80 nm or more, 90 nm or more, 100 nm or more, 120 nm or more, 140 nm or more, 160 nm or more, 180 nm or more, 200 nm or more, 250 nm or more, or even more). For each opening 806, the minimum opening dimension can be 1 micron or less (e.g., 900 nm or less, 850 nm or less, 800 nm or less, 750 nm or less, 700 nm or less, 650 nm or less, 600 nm or less, 550 nm or less, 500 nm or less, 450 nm or less, 400 nm or less, or even less).

The distribution of minimum opening dimensions among openings 806 can have a full-width at half-maximum (FWHM) value of 500 nm or less (e.g., 450 nm or less, 400 nm or less, 350 nm or less, 300 nm or less, 250 nm or less, 200 nm or less, 150 nm or less, 100 nm or less, 75 nm or less, 50 nm or less, 40 nm or less, 30 nm or less, 20 nm or less, 15 nm or less, 10 nm or less, or even less).

In general, the opening 808 of each channel 804 in second surface 606 has a minimum opening dimension corresponding to the shortest distance spanning the opening and passing through the center of mass of the opening. For each opening 808, the minimum opening dimension can be within any of the limits and ranges described above in connection with openings 806. Similarly, the distribution of minimum opening dimensions among openings 808 can have a full-width at half-maximum (FWHM) value within any of the limits or ranges describe above in connection with openings 806.

In some embodiments, the openings 806 of channels 804 in filter member 602 are distributed irregularly on first surface 604 of filter member 602. In certain embodiments, the openings 806 are distributed in a more regularized fashion. For example, the openings 806 can be distributed according to a regular pattern, and can form a rectangular array, a hexagonal array, or any other type of array pattern on first surface 604. In some embodiments, a mean spacing between the centers of mass of openings 806 in first surface 604 is between 20 nm and 5 microns (e.g., between 30 nm and 5 microns, between 40 nm and 5 microns, between 50 nm and 5 microns, between 75 nm and 5 microns, between 100 nm and 5 microns, between 50 nm and 4 microns, between 50 nm and 3 microns, between 50 nm and 2 microns, between 100 nm and 4 microns, between 100 nm and 3 microns, between 100 nm and 2 microns, between 250 nm and 4 microns, between 250 nm and 3 microns, between 250 nm and 2 microns, between 250 nm and 1 micron, between 500 nm and 4 microns, between 500 nm and 3 microns, between 500 nm and 2 microns, between 1 micron and 4 microns, between 1 micron and 3 microns, or any other range within the foregoing ranges).

Figure 8C:
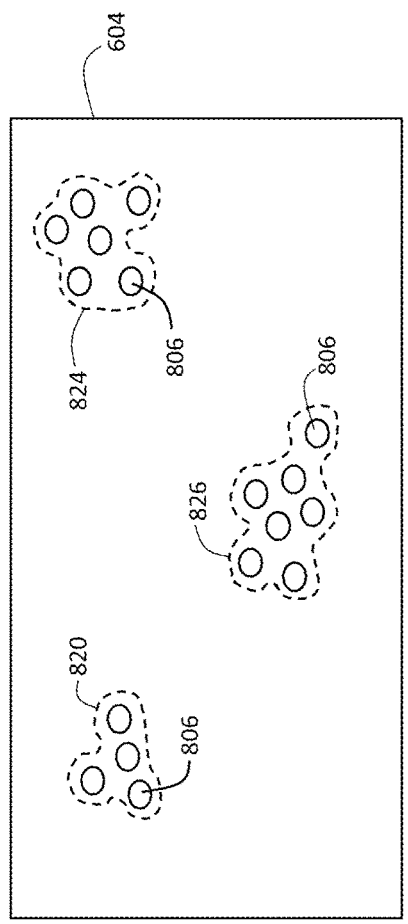
FIG. 8C is a schematic diagram of a portion of a surface of a filter member.

FIG. 8C is a schematic diagram showing a portion of first surface 604 that includes openings 806 for a plurality of channels 804 formed in the filter member. The openings 806 are clustered in multiple groups 820, each of which is indicated by a dashed line enclosing members of the group. For first surface 604 with a plurality of openings 806, each opening has a minimum opening dimension corresponding to the shortest distance spanning the opening and passing through the center of mass of the opening. For the plurality of openings 806 in the first surface 604, there is a mean value of the minimum opening dimension.

In general, a given opening 806 is part of a group if a distance between the center of mass of the opening and the center of mass of another opening in the group is less than twice the value of the mean minimum opening dimension for first surface 604. For the groups 820 of openings 806 in first surface 604, a center of each group can be defined as the point which represents the shortest sum of distances to the centers of mass of each opening in the group. Among the groups 820, a mean center-to-center spacing among nearest-neighbor groups can be larger than the mean minimum opening dimension for first surface 604 by a factor of 2.5 or more (e.g., 3.0 or more, 3.5 or more, 4.0 or more, 4.5 or more, 5.0 or more, 5.5 or more, 6.0 or more, 7.0 or more, 8.0 or more, 8.5 or more, 9.0 or more, 10.0 or more, 12.0 or more, 15.0 or more, or even more).

In some embodiments, as shown in FIG. 8B for example, one or more channels 804 are oriented such that an axis of the channels 804 is oriented approximately parallel to a direction of fluid flow through filter member 602. It has been discovered, however, that by orienting at least some of channels 804 such that their respective channel axes are inclined relative to the bulk direction of fluid flow through filter member 602, the rate of fouling of the filter member can be significantly reduced, and therefore the elapsed time before the filter member is due for replacement can be significantly extended. Without wishing to be bound by theory, it is believed that by inclining the channel axes relative to the bulk direction of fluid flow, the trapping of viral particles in enhanced due to increased interactions with the viral particles along the lengths of the channels.

Figure 9B:
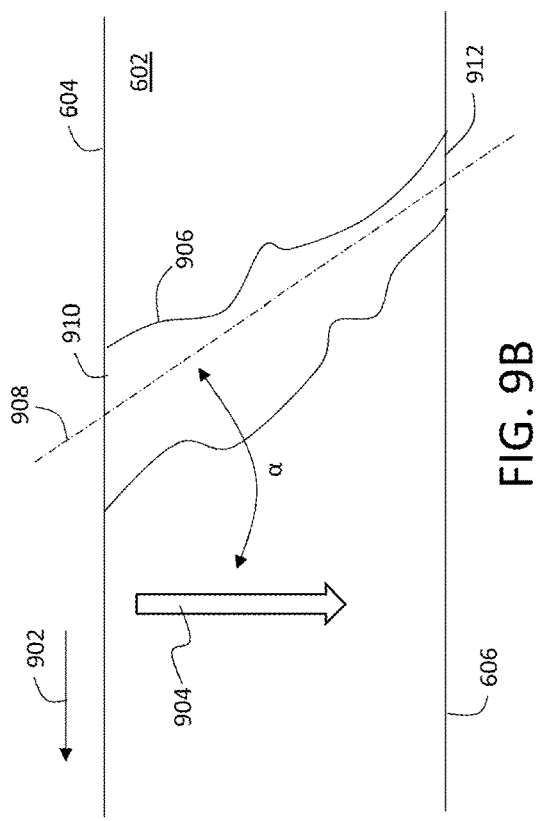
FIG. 9B is a schematic cross-sectional diagram of another example of a filter member with an inclined channel.
Figure 9A:
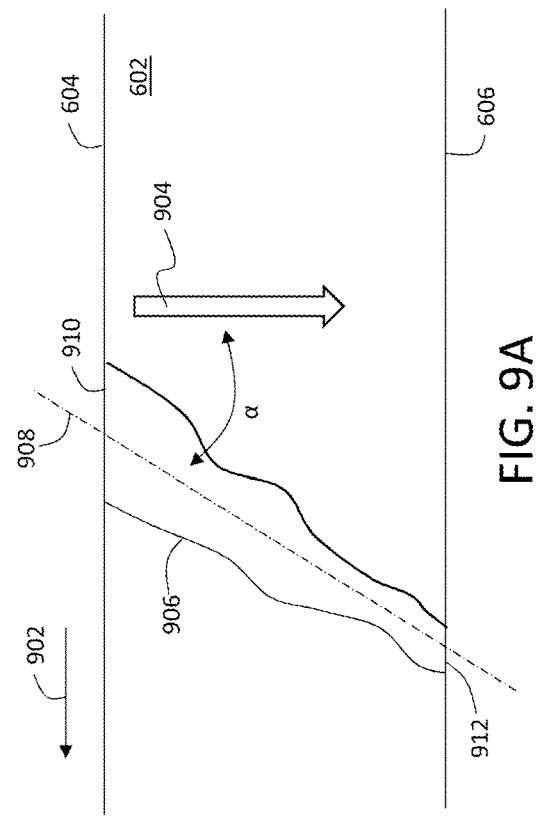
FIG. 9A is a schematic cross-sectional diagram of an example of a filter member with an inclined channel.

FIG. 9A is a schematic diagram of a filter member 602 with an inclined channel. In FIG. 9A, the crossflow direction (i.e., within a filter unit) is indicated by arrow 902, and the direction of bulk fluid flow within filter member 602—which is tangential to crossflow direction 902—is indicated by arrow 904. The direction of bulk fluid flow is nominally orthogonal to first surface 604 and second surface 606 of filter member 602.

Channel 906 is formed in filter member 602, and has openings 910 and 912 in surfaces 604 and 606, respectively. A channel axis 908 extends between the centers of mass of openings 910 and 912). Channel axis 908 is inclined at an angle $\alpha$ relative to the direction of bulk fluid flow 904.

In some embodiments, the fraction of channels within filter member 602 that are inclined relative to the direction of bulk fluid flow is 20% or more (e.g., 30% or more, 40% or more, 50% or more, 60% or more, 70% or more, 75% or more, 80% or more, 85% or more, 90% or more, 95% or more, 97% or more, 98% or more, 99% or more, or even 100%). For a given channel 906, the angle $\alpha$ can be 5 degrees or more (e.g., 10 degrees or more, 15 degrees or more, 20 degrees or more, 25 degrees or more, 30 degrees or more, 35 degrees or more, 40 degrees or more, 45 degrees or more, 50 degrees or more, or even more). Alternatively, or in addition, the angle $\alpha$ can be 90 degrees or less (e.g., 89 degrees or less, 88 degrees or less, 87 degrees or less, 86 degrees or less, 85 degrees or less, 80 degrees or less, 75 degrees or less, 70 degrees or less, 65 degrees or less, 60 degrees or less, or even less). The angle $\alpha$ can be between 1 degree and 90 degrees (or any smaller range within this range).

In certain embodiments, among the channels 906 within a filter member, a mean value of the angle of inclination $\alpha$ of the channels relative to the direction of bulk fluid flow 904 is 5 degrees or more (e.g., 10 degrees or more, 15 degrees or more, 20 degrees or more, 25 degrees or more, 30 degrees or more, 35 degrees or more, 40 degrees or more, 45 degrees or more, 50 degrees or more, or even more). Alternatively, or in addition, the angle $\alpha$ can be 90 degrees or less (e.g., 89 degrees or less, 88 degrees or less, 87 degrees or less, 86 degrees or less, 85 degrees or less, 80 degrees or less, 75 degrees or less, 70 degrees or less, 65 degrees or less, 60 degrees or less, or even less). The angle $\alpha$ can be between 1 degree and 90 degrees (or any smaller range within this range).

In some embodiments, for channels 906 that are inclined relative to the direction of bulk fluid flow 904, a full-width at half-maximum (FWHM) of the distribution of angles $\alpha$ can be between 0 degrees and 60 degrees. For example, the FWHM of the distribution can be 60 degrees or less (e.g., 50 degrees or less, 40 degrees or less, 30 degrees or less, 20 degrees or less, 15 degrees or less, 10 degrees or less, 5 degrees or less).

In FIG. 9A, channel 906 is inclined toward the crossflow direction 902. However, in certain embodiments, one or more of the channels formed in filter member 602 can be inclined away from crossflow direction 902 (i.e., in an anti-clockwise direction in FIG. 9A) relative to bulk fluid flow direction 904. FIG. 9B is a schematic diagram showing a filter member 602 with a channel 906 inclined away from crossflow direction 902. The included angle between bulk fluid flow direction 904 and channel axis 908 is α. The various features discussed above in connection with FIG. 9A apply in a similar manner to channel 906 in FIG. 9B.

In some embodiments, the fraction of channels in a filter member 602 that are inclined away from the crossflow direction is 20% or more (e.g., 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, 97% or more, 98% or more, 99% or more, or even more). It has been discovered that in some embodiments, orienting the filter member 602 such that some or all of the channels are inclined away from the crossflow direction can further increase the useful lifetime of the filter member by reducing the rate at which viral particles desorb from internal binding sites within the channels and break through the second surface 606 of the filter member.

It should be noted that in FIG. 9A, channel 906 does not undulate or weave back and forth through filter member 602. However, in some embodiments, channels in a filter member can extend in multiple directions—for example, by undulating back and forth—relative to the direction of bulk fluid flow. However, the foregoing considerations apply to such channels as well, with the channel axis and angle of inclination defined in the same manner.

In some embodiments, for a particular channel having a channel axis that is either inclined or parallel to the direction of bulk fluid flow, the channel can be partially obscured or occluded at or near the channel opening. FIG. 10 is a schematic diagram of a filter member 602 that includes a channel 1006. Channel 1006 has a maximum cross-sectional dimension w as shown in the figure. However, at opening 1010, the maximum cross-sectional dimension is $w_o$, which is smaller than w. The ratio of $w_o$/w can generally be selected as desired to yield an obscured channel 1006. In some embodiments, for example, the ratio $w_0$/w is 0.98 or less (e.g., 0.97 or less, 0.96 or less, 0.95 or less, 0.94 or less, 0.93 or less, 0.92 or less, 0.91 or less, 0.90 or less, 0.85 or less, 0.80 or less, 0.75 or less, 0.70 or less, 0.65 or less, 0.60 or less, 0.55 or less, 0.50 or less, 0.45 or less, 0.40 or less, 0.35 or less, 0.30 or less, 0.25 or less, 0.20 or less, or even less).

In certain embodiments, the obscuration of the channel opening in first surface 604 is measured relative to a location just below first surface 604. For example, referring again to FIG. 10, $w_n$ is the maximum cross-sectional dimension of channel 1006 at a location 10% of the distance between first surface 604 and second surface 606. For a partially obscured channel 1006, $w_n$ can be larger than $w_0$. In some embodiments, for example, the ratio $w_0$/$w_n$ is 0.99 or less (e.g., 0.97 or less, 0.96 or less, 0.95 or less, 0.94 or less, 0.93 or less, 0.92 or less, 0.91 or less, 0.90 or less, 0.85 or less, 0.80 or less, 0.75 or less, 0.70 or less, 0.65 or less, 0.60 or less, 0.55 or less, 0.50 or less, 0.45 or less, 0.40 or less, 0.35 or less, 0.30 or less, 0.25 or less, 0.20 or less, or even less).

To improve retention of viral particles, the interior surfaces of the channels can be structured to increase their surface area, providing adsorption sites for viral particles. It has been discovered that the ratio of the average cross-sectional area of the openings to the average surface area of the interior surfaces of the channels can be an important factor in reducing the likelihood of viral breakthrough at second surface 606, thereby extending the lifetime of filter member 602. In some embodiments, for example, the ratio of the average cross-sectional area of the openings of the channels in first surface 604 to the average surface area of the interior surfaces of the channels can be 0.05 or less (e.g., 0.04 or less, 0.03 or less, 0.02 or less, 0.01 or less, 0.005 or less, 0.003 or less, 0.001 or less, 0.0005 or less, 0.0001 or less, 0.00001 or less, 0.000001 or less, 0.0000001 or less, or even less).

In some embodiments, to further increase the surface area of the interior surfaces of the channels, some or all of the channels can include lateral projections. FIG. 11 is a schematic diagram of a filter member 602 that includes a channel 1102 with openings 1104 and 1106 at first and second surfaces 604 and 606, respectively, and five lateral projections 1108. Channel 1102 has a channel axis 1110 that connects the centers of mass of openings 1104 and 1106. The length of channel axis 1110 is L, measured between the centers of mass of openings 1104 and 1106.

An extension or protrusion of channel 1102 is defined as a "lateral projection" for purposes of this disclosure if the extension or protrusion does not reach second surface 606, and if the perpendicular distance $w_p$ from axis 1110 to the furthest point of the extension or protrusion away from axis 1110 is 0.05 L or more. The perpendicular distances $w_p$ are shown in FIG. 11 for each of the lateral projections.

In general, for a given lateral projection, $w_p$ can be 0.05 L or more (e.g., 0.10 L or more, 0.20 L or more, 0.30 L or more, 0.40 L or more, 0.50 L or more, 0.75 L or more, 1.0 L or more, 1.25 L or more, 1.5 L or more, 2.0 L or more, 2.5 L or more, 3.0 L or more, 3.5 L or more, 4.0 L or more, 5.0 L or more, or even more).

A given channel 1102 can include any number of lateral projections (e.g., none, 1 or more, 2 or more, 3 or more, 4 or more, 5 or more, 6 or more, 7 or more, 8 or more, or even more). Primary projections extending from the channel axis 1110 can also include secondary projections extending from the primary projections, such that individual channels have a branched, "tree-like" structure. Within a filter member 602, a mean number of lateral projections per channel 1102 can be none, or 0.25 or more (e.g., 0.50 or more, 1.0 or more, 1.5 or more, 2.0 or more, 2.5 or more, 3.0 or more, 3.5 or more, 4.0 or more, 4.5 or more, 5.0 or more, 5.5 or more, 6.0 or more, 6.5 or more, 7.0 or more, 7.5 or more, 8.0 or more, or even more).

In some embodiments, channels in a filter member can include one or more coating materials. Coating materials can be used, for example, to enhance the adsorption of viral particles, and to promote fluid flow through the member. Coatings can also be used to adjust the hydrophobic or hydrophilic character of the member, and/or to adjust ionic characteristics of the member. In general, individual channels in a filter member can include no coating layer, a single coating layer, or multiple (e.g., 2 or more, 3 or more, 4 or more, 5 or more, or even more) coating layers. FIG. 12 is a schematic diagram showing a filter member 602 that includes a channel 1202 with two coating layers 1204 and 1206. Each of the coating layers conforms to the internal channel surface in FIG. 12. A variety of different coating materials can be used. Examples of such materials include, but are not limited to, celluloses and regenerated celluloses, hydrophilic polymers (e.g., polyethersulfones, polyethyleneglycols), hydrophobic polymers (i.e., polyethylenes, polypropylenes, polyvinyl benzenes), polypropylene glycols, other polyols, polyurethanes, polymethyl methacrylates, and polyacrylic acids.

Typically, coating layers applied to the walls of channels in the filter member are relatively thin. For example, for a filter member with multiple channels, each channel has a maximum cross-sectional dimension measured in a plane orthogonal to the direction of fluid flow in the filter member, and the filter member has an average maximum cross-sectional dimension among all such channels. In some embodiments, a ratio of the average thickness of a coating material applied to internal surfaces of the channels to the average maximum cross-sectional dimension of the channels is 0.2 or less (e.g., 0.15 or less, 0.10 or less, 0.05 or less, 0.04 or less, 0.03 or less, 0.02 or less, 0.01 or less, 0.005 or less, 0.004 or less, 0.003 or less, 0.002 or less, 0.001 or less).

Multi-Layer Filters

Figure 13:
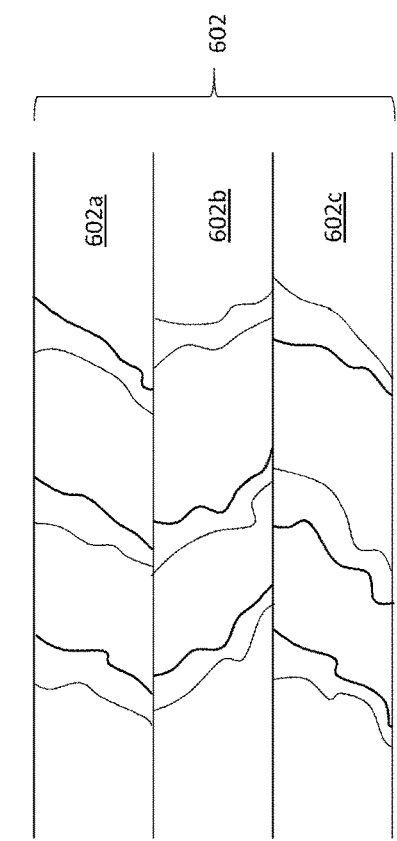
FIG. 13 is a schematic cross-sectional diagram of an example of a filter member that includes multiple layers of channels.
Figure 12:
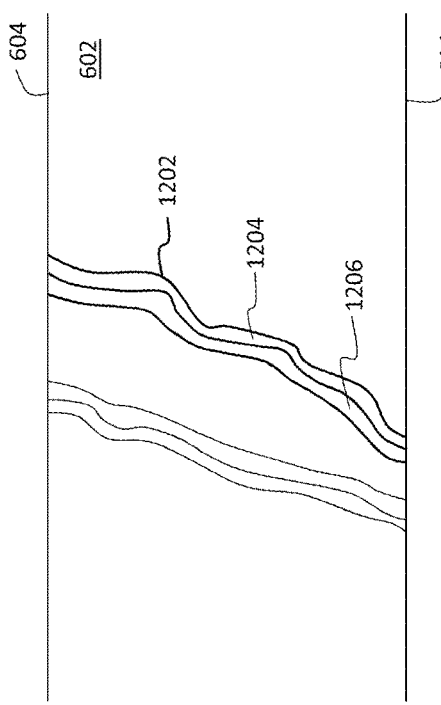
FIG. 12 is a schematic cross-sectional diagram of an example of a filter member that includes a channel with coating layers.

In some embodiments, filter member 602 can be multi-layered, and can effectively be formed from two or more filter members in contact. FIG. 13 is a schematic diagram showing a filter member 602 formed by three layers 602a-c. Although three layers are shown in FIG. 13, more generally filter member 602 can be formed by 2 or more (e.g., 3 or more, 4 or more, 5 or more, 6 or more, 7 or more, 8 or more, 9 or more, 10 or more, or even more) layers.

Layers 602a-c can each have any of the properties described above. In other words, any of the thicknesses, layer and channel geometries, and other attributes discussed herein can be present in any one or more of layers 602a-c. Between any two layers 602a-c, one or more of the channels formed in the upstream layer can be in direct fluid communication with one or more of the channels in the downstream layer. In this context, "direct fluid communication" means that Multi-layered filter members can provide advantages in a number of different operating environments. For example, in some embodiments, the first layer 602a can have a relatively small number of openings per unit area, with a relatively smooth surface texture. This configuration allows fluid moving in the crossflow direction across the surface of first layer 602a to effectively "sweep" the surface clean, preventing build-up of solid matter on the surface that would otherwise impede effective filtration. In certain embodiments, the second layer 602b can be relatively porous, with a relatively large number of channels for trapping viral particles, and as a consequence, a comparatively rough texture. In some embodiments, the third layer 602c can have relatively small openings at the second surface (for example, openings where the maximum cross-sectional dimension is between about 20 nm and 30 nm), so that the third layer acts as effectively a size cutoff filter for particles in the fluid.

Fiber Geometry

As discussed above, filter member 602 is typically implemented as a layer in contact with a hollow fiber through which process fluid flows. In general, the outer diameter of the combination of the hollow fiber and filter member 602 can generally be selected as desired to ensure adequate crossflow and tangential flow through the filter unit. In some embodiments, for example, the outer diameter can be 0.3 mm or more (e.g., 0.4 mm or more, 0.5 mm or more, 0.6 mm or more, 0.7 mm or more, 0.8 mm or more, 0.9 mm or more, 1.0 mm or more, 1.1 mm or more, 1.2 mm or more, 1.3 mm or more, 1.4 mm or more, 1.5 mm or more).

The inner diameter of the hollow fiber can also be selected as desired. In some embodiments, for example, the inner diameter of the hollow fiber is 0.1 mm or more (e.g., 0.2 mm or more, 0.3 mm or more, 0.4 mm or more, 0.5 mm or more, 0.6 mm or more, 0.7 mm or more, 0.8 mm or more, 0.9 mm or more, 1.0 mm or more, or even more). The inner diameter of the hollow fiber can be smaller than the outer diameter of the combination of the hollow fiber and filter member 602 by 0.001 mm or more (e.g., 0.005 mm or more, 0.01 mm or more, 0.012 mm or more, 0.014 mm or more, 0.016 mm or more, 0.018 mm or more, 0.020 mm or more, 0.022 mm or more, 0.024 mm or more, 0.026 mm or more, 0.028 mm or more, 0.030 mm or more, 0.032 mm or more, 0.034 mm or more, 0.036 mm or more, 0.038 mm or more, 0.040 mm or more, 0.042 mm or more, 0.044 mm or more, 0.046 mm or more, 0.048 mm or more, 0.05 mm or more, 0.055 mm or more, 0.060 mm or more, 0.065 mm or more, 0.070 mm or more, 0.075 mm or more, 0.080 mm or more, 0.085 mm or more, 0.090 mm or more, 0.10 mm or more, or even more).

Laminar Tangential Flow Viral Filtration

In the foregoing discussion, tangential flow viral filtration is performed using a hollow fiber-based filter unit. Commercially available viral filters are implemented in this manner, and used in non-recirculating filtration assemblies. However, the filter members described herein can also be used in laminar tangential filtration sub-systems to implement tangential flow viral filtration. Such sub-systems have a number of advantages relative to fiber-based filtration. First, laminar filter members are typically easier to fabricate than tubular filter members. Second, laminar filter members can be produced with relatively large surface areas, and can therefore accommodate a larger flux of process fluid than fiber-based filter members. Third, laminar filter units can include a turbulence promoter (such as a screen) that yields turbulent fluid flow across the filter member, thereby helping to "sweep" the surface of the filter member via cross-flowing process fluid.

Figure 14:
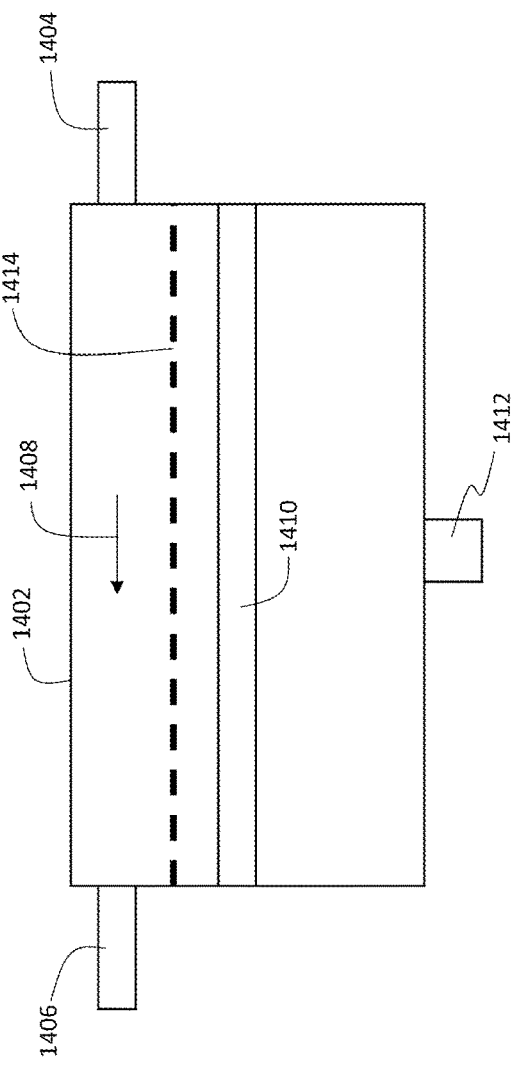
FIG. 14 is a schematic diagram of an example of a laminar tangential viral filtration unit.

FIG. 14 is a schematic diagram showing an example of a laminar tangential viral filtration unit 1402. Unit 1402 includes an inlet 1404, and outlet 1406, a filter member 1410, a product stream outlet 1412, and a screen 1414 that functions as a turbulence promoter. During operation, process fluid enters inlet 1404 and flows in the direction shown by arrow 1408 to outlet 1406. When the cross-flowing process fluid interacts with screen 1414, turbulence is created in the flowing process fluid, which helps to dislodge solid matter from the surface of filter member 1410.

Trans-membrane pressure within the unit drives a portion of the process fluid through filter member 1410, generating a product stream that leaves the filter member through product stream outlet 1412. The product stream is generally free from viral particles, which remain trapped within filter member 1410.

In general, filter member 1410 can have any of the features described above in connection with filter member 602. That is, any of the thicknesses, layer and channel geometries, and other attributes discussed herein can be present in layer 1410.

OTHER EMBODIMENTS

It is to be understood that the foregoing description is intended to illustrate and not limit the scope of the disclosure, and embodiments other than those expressly described are within the scope of the disclosure.

What is claimed is:

1. A method for removing viral particles from a solution, the method comprising:
    (a) transporting a solution comprising viral particles through a filter unit comprising a filter member;
    (b) capturing a portion of the solution that passes through a filter member in a direction orthogonal to a flow direction of the transported solution through the filter unit;
    (c) transporting a remaining portion of the solution that does not pass through the filter member into a reservoir;
    (d) recirculating a portion of the solution from the reservoir through the filter unit; and (e) repeating steps (b)-(d) to capture multiple portions of the solution, where each captured solution passes through the filter member, wherein the filter member has a thickness and comprises a plurality of channels, and wherein for each of at least 50% of the channels in the filter member, a channel axis is oriented at an angle of between 5 degrees and 85 degrees relative to a thickness direction of the filter member.

2. The method of claim 1, wherein transporting the remaining portion of the solution that does not pass through the filter member into the reservoir comprises pumping the remaining portion of the solution into the reservoir.

3. The method of claim 1, wherein recirculating the portion of the solution from the reservoir through the filter unit comprises applying a fluid pressure to the reservoir to drive transport of the portion of the solution from the reservoir to the filter unit.

4. The method of claim 3, further comprising maintaining a constant applied fluid pressure to the reservoir during transport of the portion of the solution from the reservoir to the filter unit.

5. The method of claim 4, further comprising maintaining the constant applied fluid pressure to the reservoir to recirculate each portion of the solution from the reservoir through the filter unit.

6. The method of claim 1, wherein the filter unit has a cylindrical shape and wherein the filter member has a tubular shape.

7. The method of claim 6, wherein the captured portion of the solution passes through the filter member in one or more radial directions of the filter unit.

8. The method of claim 1, wherein each of the plurality of channels comprises an opening at a first surface of the filter member, and wherein a ratio of a total area of the openings to a total area of the first surface is 0.10 or more.

9. The method of claim 8, wherein the filter member is tubular, and wherein the first surface of the filter member is an inner surface of the tubular filter member.

10. The method of claim 1, wherein each of the plurality of channels has a volume, and wherein a ratio of a total volume of the channels to a total volume of the filter member is 0.05 or more.

11. The method of claim 1, wherein each of at least some channels of the plurality of channels comprises an opening at a first surface of the filter member having a first cross-sectional area in the first surface, and the first cross-sectional area is smaller than a second cross-sectional area of the channel at a location between the first surface and a second surface of the filter member.

12. The method of claim 11, wherein the filter member is tubular, and wherein the first surface of the filter member is an inner surface of the tubular filter member.

13. The method of claim 11, wherein a ratio of the first cross-sectional area to the second cross-sectional area is 0.95 or less.

14. The method of claim 11, wherein the at least some channels comprise at least 40% of the plurality of channels.

15. The method of claim 1, wherein the channel axes of the plurality of channels comprise a distribution of orientations relative to the thickness direction of the filter member, and wherein an average orientation of the distribution is a member selected from the group consisting of: between 10 degrees and 30 degrees relative to the thickness direction; between 30 degrees and 50 degrees relative to the thickness direction; and between 50 degrees and 80 degrees relative to the thickness direction.

16. The method of claim 1, wherein each of at least some channels of the plurality of channels comprises one or more secondary channels extending from the channel axis.

17. The method of claim 1, wherein the filter member is formed from a first material, and wherein each of at least some channels of the plurality of channels comprises a second material positioned on an interior surface of the channel.

18. The method of claim 17, wherein a ratio of an average thickness of the second material on the interior surface of the at least some channels to a maximum cross-sectional dimension of the at least some channels is 0.2 or less.

19. The method of claim 1, wherein the plurality of channels is a first plurality of channels, and wherein the filter member comprises:
a first layer comprising the first plurality of channels; and
a second layer comprising a second plurality of channels.

20. The method of claim 19, wherein an average orientation of axes of the first plurality of channels relative to the thickness direction of the filter member is different from an average orientation of axes of the second plurality of channels relative to the thickness direction of the filter member.

* * * * *